United States Patent [19]
Tong et al.

[11] Patent Number: 5,944,598
[45] Date of Patent: Aug. 31, 1999

[54] METHOD AND APPARATUS FOR USING IMAGE ANALYSIS TO DETERMINE MEAT AND CARCASS CHARACTERISTICS

[75] Inventors: Alan Kwai-Wah Tong, Lacombe; David John Robinson; Tong Liu, both of Edmonton, all of Canada

[73] Assignees: Her Majesty the Queen in right of Canada as represented by the Department of Agriculture; Agri-Food Canada, Lacombe, both of Canada

[21] Appl. No.: 08/914,560

[22] Filed: Aug. 19, 1997

Related U.S. Application Data

[60] Provisional application No. 60/024,310, Aug. 23, 1996.

[51] Int. Cl.$^6$ .............................. A22C 18/00; B07C 3/18
[52] U.S. Cl. .............................................. 452/158; 358/93
[58] Field of Search .................................... 452/158, 157; 358/93

[56] References Cited

U.S. PATENT DOCUMENTS

| | | |
|---|---|---|
| 3,154,625 | 10/1964 | Kail . |
| 3,735,247 | 5/1973 | Harker . |
| 3,800,363 | 4/1974 | Lapeyre . |
| 4,226,540 | 10/1980 | Barten et al. . |
| 4,413,279 | 11/1983 | Gorl . |
| 4,439,037 | 3/1984 | Northeved et al. ...................... 358/93 |
| 4,461,575 | 7/1984 | Miller et al. . |
| 4,738,004 | 4/1988 | Lapeyre . |
| 4,745,472 | 5/1988 | Hayes . |

(List continued on next page.)

FOREIGN PATENT DOCUMENTS

| | | |
|---|---|---|
| 0 321 981 A1 | 6/1989 | European Pat. Off. . |
| 0 523 865 A1 | 1/1993 | European Pat. Off. . |
| 44 08 604A1 | 12/1995 | Germany . |
| WO 91/14180 | 9/1991 | WIPO . |
| WO 92/00523 | 1/1992 | WIPO . |
| WO 93/21597 | 10/1993 | WIPO . |
| WO 94/00997 | 1/1997 | WIPO . |

OTHER PUBLICATIONS

Benson, K. Blair, et al. 1992. Television Engineering Handbook. Rev. ed. McGraw–Hill Inc., New York.
Jones, S.D.M., et al. 1993. Technical Report—Instrument Beef Grading.
Richmond, R.J., et al. 1995. Technical Report—Instrument Beef Grading (An Evalution of Video Image Analysis).
Gonzalez, Rafael C., et al. 1992. Digital Image Processing. Addison–Wesley Publishing Company. Section 4.2; Chapter 7; Section 8.1.2 and Section 8.4.

*Primary Examiner*—Willis Little
*Attorney, Agent, or Firm*—Greenlee, Winner & Sullivan, P.C.

[57] ABSTRACT

In a process and apparatus for determining grading parameters of a carcass, the outline of an image of the carcass is traced and reference points representing anatomical features of the carcass are identified. Second reference points being located at pre-determined positions relative to the first reference points are then identified. The carcass image is divided into a plurality of sections, the boundaries of each section being determined as a function of the position of the first and second reference points, and the area of each section is determined. A grading parameter predictive equation is determined wherein the grading parameter is included as a dependent variable, and at least one area of a carcass image section is included as an independent variable. Solving the predictive equation provides a value for the grading parameter of the carcass. Other measurements which can be obtained from the carcass image and used as independent variables in predictive equations include distances from dorsal and ventral regions of the carcass image outline to a carcass mid-line, carcass widths, angular measurements between reference points, and measurements of curvature of the carcass image outline. Improved rib eye tracing techniques permit accurate measurement of rib eye parameters. The measured rib eye parameters may be used to determine a quality grade for the carcass or as independent variables in a carcass grading parameter predictive equation, alone, or in conjunction with measurements taken from the carcass image.

27 Claims, 12 Drawing Sheets

U.S. PATENT DOCUMENTS

| | | |
|---|---|---|
| 4,785,817 | 11/1988 | Stouffer ............................... 128/660.07 |
| 4,879,752 | 11/1989 | Aune et al. . |
| 4,916,629 | 4/1990 | Bogue et al. . |
| 4,939,574 | 7/1990 | Petersen et al. . |
| 5,194,036 | 3/1993 | Chevalier et al. ...................... 452/157 |
| 5,324,228 | 6/1994 | Vogeley . |
| 5,334,084 | 8/1994 | O'Brien et al. ......................... 452/157 |
| 5,335,790 | 8/1994 | Geiger et al. . |
| 5,339,815 | 8/1994 | Yujun et al. . |
| 5,352,153 | 10/1994 | Burch et al. . |
| 5,412,220 | 5/1995 | Moore . |
| 5,458,418 | 10/1995 | Jones et al. ............................... 374/45 |
| 5,470,274 | 11/1995 | Kadi et al. ............................. 452/158 |
| 5,474,085 | 12/1995 | Hurnik et al. . |
| 5,483,441 | 1/1996 | Scofield . |
| 5,576,949 | 11/1996 | Scofield et al. . |
| 5,668,634 | 9/1997 | Newman .................................. 452/157 |

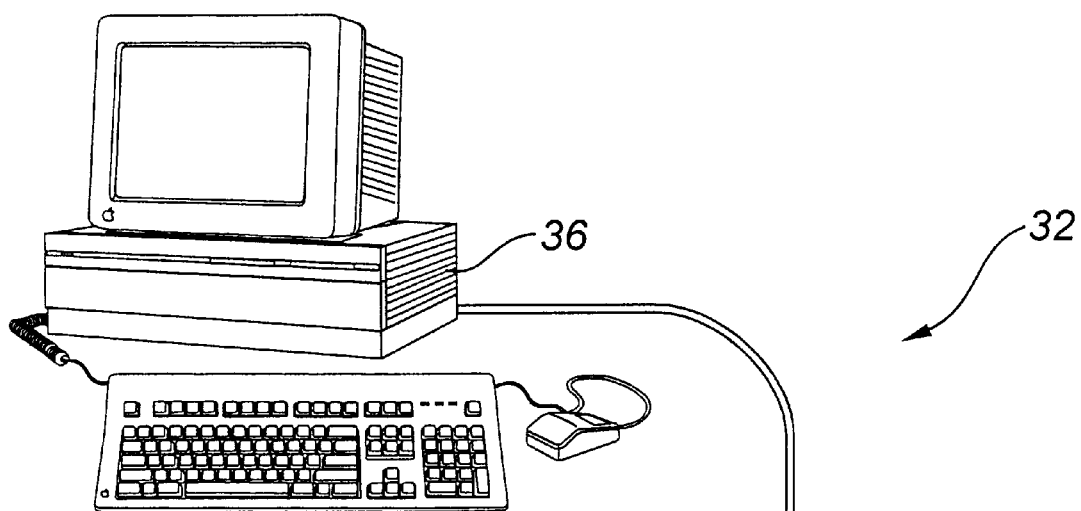
FIG. 2.
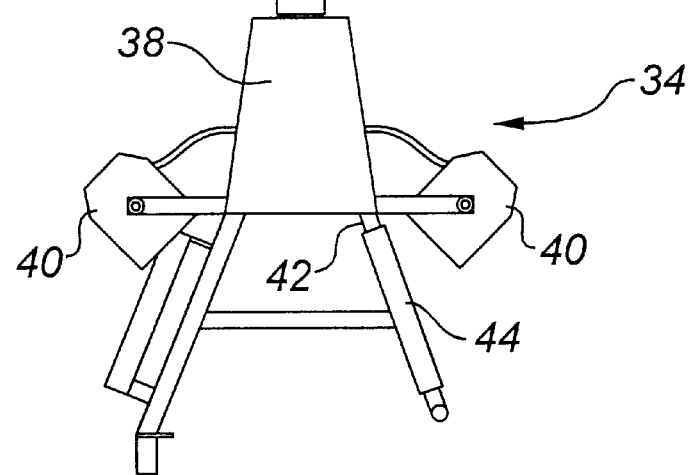
FIG. 3.
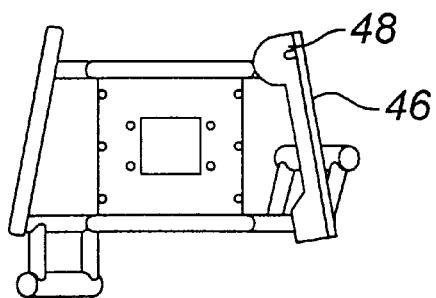

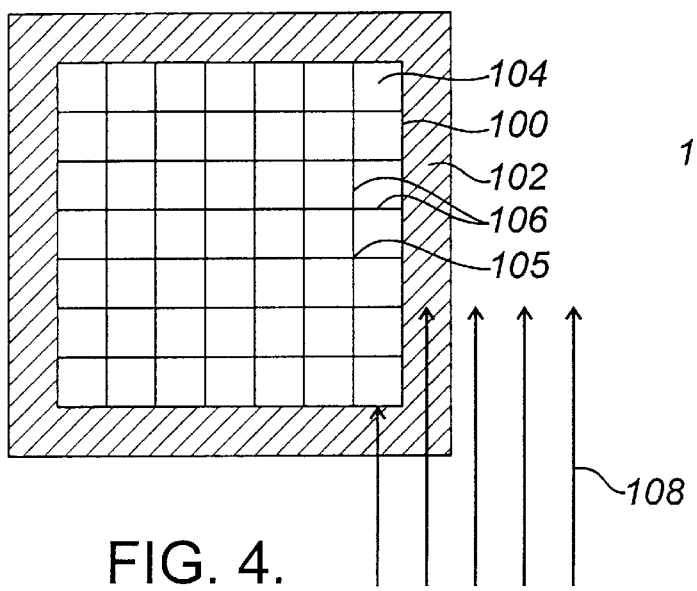
FIG. 4.
FIG. 5.
FIG. 6.
FIG. 7.
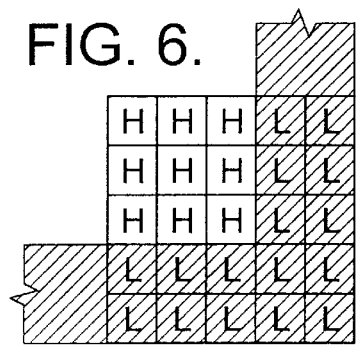
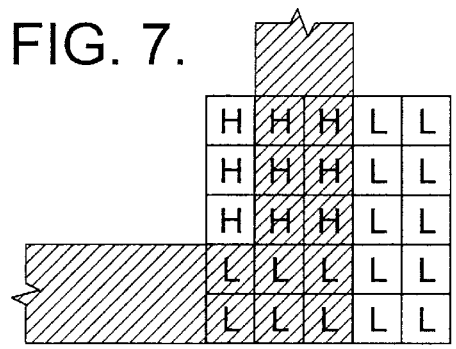
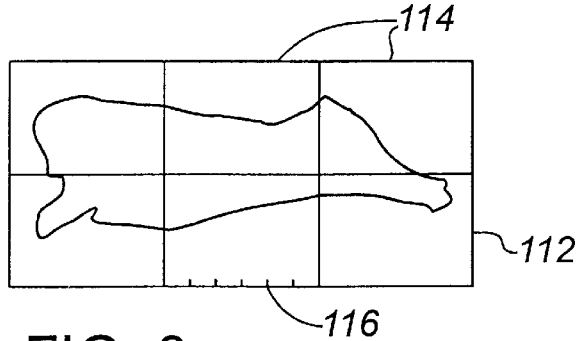
FIG. 8.
FIG. 9.

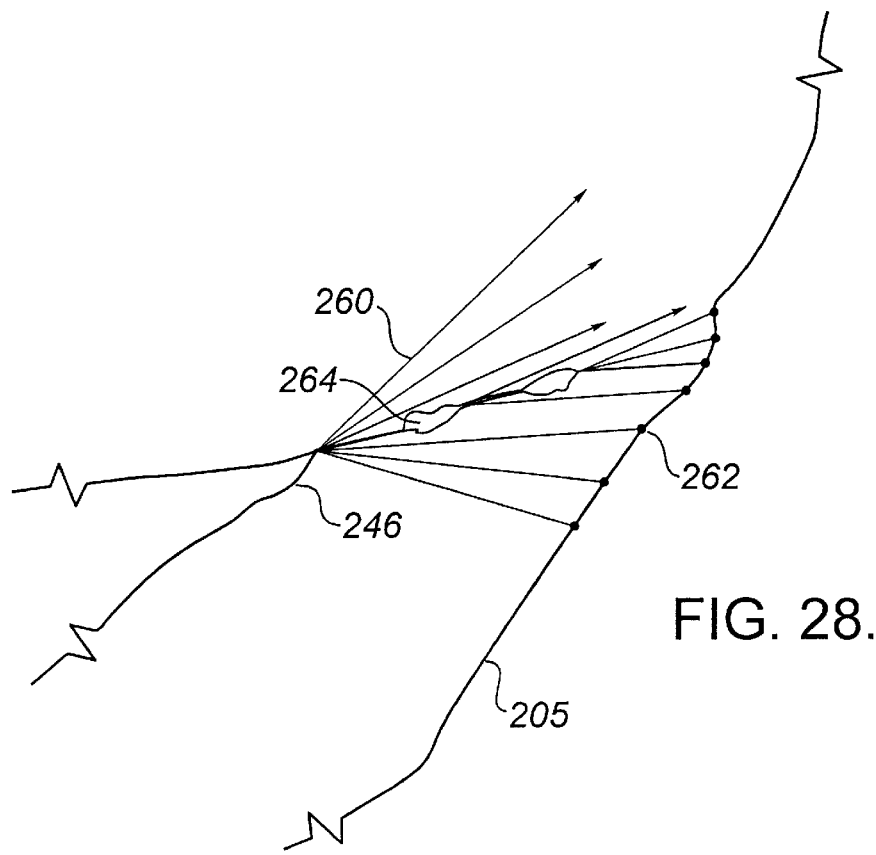
FIG. 28.
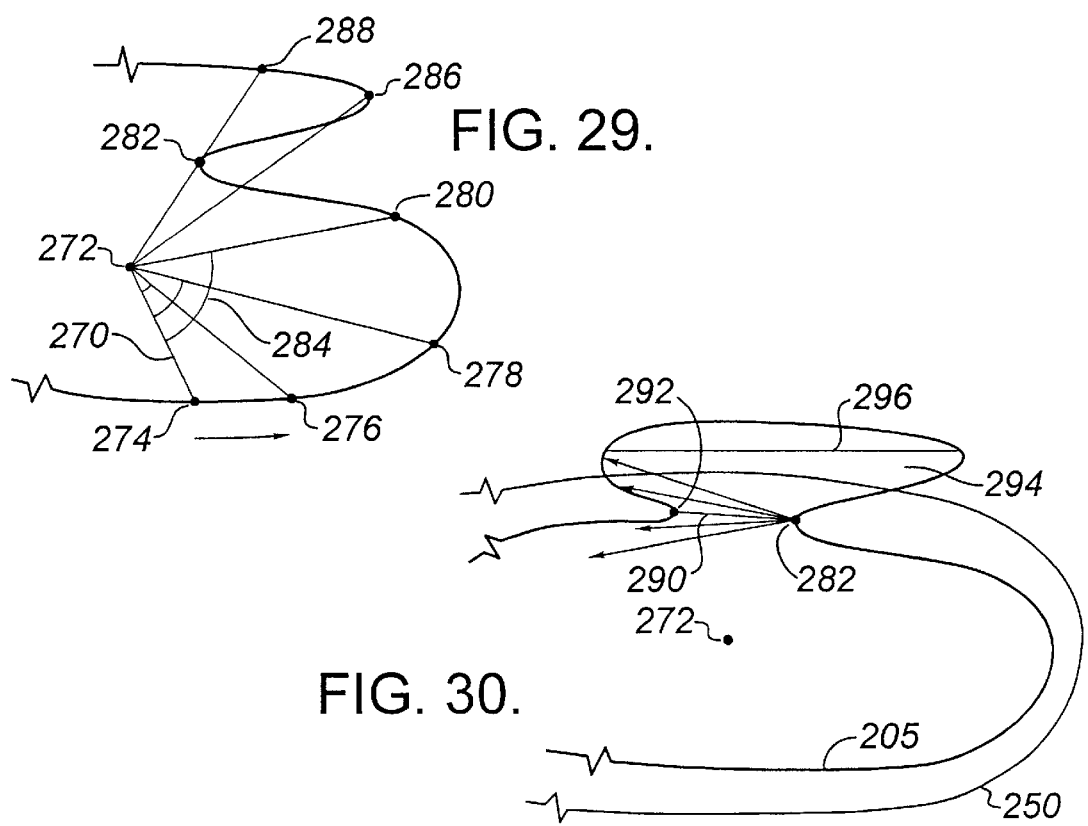
FIG. 29.
FIG. 30.

METHOD AND APPARATUS FOR USING IMAGE ANALYSIS TO DETERMINE MEAT AND CARCASS CHARACTERISTICS

CROSS REFERENCE TO RELATED APPLICATIONS

This application takes priority from U.S. provisional application Ser. No. 60/024,310, filed Aug. 23, 1996, which is incorporated in its entirety herein.

BACKGROUND OF THE INVENTION

1. Field of the Invention

The invention relates to image processing and statistical analysis of digitized images of carcasses of meat animals to determine grade and yield parameters of the carcass.

2. Description of the Related Art

Meat animal grading, in both live animals and carcasses, has typically been performed by human graders, introducing substantial subjectivity to the grading process. There are two main aspects to meat grading, quality grade and yield grade. Quality grade of young animals is determined by the amount of intramuscular fat (marbling) in the meat. Yield grade describes the proportion of lean tissue in the carcass.

In the carcass, grading is usually conducted by observation and measurement of a cross-section of the longissimus dorsi (described in beef as the "rib eye muscle" and in hogs as the "loin eye muscle"). Quality grade or marbling is typically determined by comparing the appearance of the rib eye with reference photographs of rib eyes of carcasses of known quality grades. The grader can assess the quality grade by comparing the amount of marbling in the rib eye being examined with the amount of marbling seen in the reference photographs.

The proportion of lean tissue in the carcass (yield grade) is typically estimated from the area of the rib eye and the thickness of subcutaneous fat at various sites around the rib eye. Yield grade calculations may also involve body cavity fat measurements and hot carcass weight. As will be discussed in greater detail herein, various definitions of a "yield grade" are possible as they may depend on particular carcass processing standards. A particularly useful measure of yield grade is the "saleable yield" of the carcass which reflects the proportion of the live weight of the animal made up by the sum of the weight of the saleable cuts plus the weight of the trim. Typically, saleable yield is determined upon butchering of the carcass into standard cuts of meat.

A number of automated meat processing systems have made use of the different light reflecting properties of muscle tissue versus fatty tissue. U.S. Pat. No. 5,324,228 (Vogeley, issued Jun. 28, 1994) describes a method and apparatus for illuminating a fish fillet with a stripe of light as it is viewed by a pair of video cameras. Light brightness signals from the cameras are converted by a computer to electric digital signals representing illumination brightness. The computer compares the digital signals to a pre-selected threshold of grey scale levels to locate peripheral fat areas. The computer then controls the operation of a cutter mechanism to remove the areas of fat. Similar systems for distinguishing light coloured edible loin meat from dark coloured inedible waste meat in tuna slices are described in U.S. Pat. No. 3,800,363 (Lapeyre, issued Apr. 2, 1974) and U.S. Pat. No. 4,738,004 (Lapeyre, issued Apr. 19, 1988).

U.S. Pat. No. 3,154,625 (Kail, issued Oct. 27, 1964) describes a method for determining the marbling of a carcass rib eye by measuring the average reflectivity of a rib eye relative to the reflectivity of a fat coloured sample plate, using a photometer.

U.S. Pat. No. 4,413,279 (Gorl, issued Nov. 1, 1983) describes an improved method for calculating a brightness threshold for distinguishing fat from lean tissue to overcome problems in identifying tissues of intermediate brightness, such as blood-smeared fat, for use in meat grading systems wherein the relative brightness of various tissues are recorded with a video camera.

U.S. Pat. No. 5,352,153 (Burch et al., issued Oct. 4, 1994) describes an apparatus for illuminating and acquiring video images of fish sections during processing.

U.S. Pat. No. 4,226,540 (Barten et al., issued Oct. 7, 1980) describes a method for determining features of meat quality in which the ratio of fat to lean tissue is determined by scanning a meat product with a moving beam of light and discriminating fat from lean tissue based on the differing brightness values of fat and tissue.

A number of video imaging grading systems have been described in which a series of images are taken of live animals. U.S. Pat. No. 5,483,441 (Scofield et al., issued Jan. 9, 1996) describes a video image acquisition and analysis system wherein a series of video images are acquired and evaluated as a live animal moves through successive fields of view. U.S. Pat. No. 4,745,472 (Hayes et al., issued May 17, 1988) describes a video image acquisition and analysis system wherein markers are placed on various anatomical reference points on the body of a live animal. The animal is then positioned in a chute having top and side walls comprising measurement grids. Video tape recordings are made of the animal in the chute, and the video information is analysed with a computer to determine the distances between the markers manually attached to the animal's body.

Other systems have combined video imaging information with other information acquired by, for instance, inserting a probe into the carcass, to provide grading information. U.S. Pat. No. 4,939,574 (Petersen et al., issued Jul. 3, 1990) describes a light-screening chamber in which the silhouette of an animal carcass is recorded with an electronic camera and the contour of the carcass determined with a data processing system. Carcass contour information is used in conjunction with a previous carcass colour assessment and meat and fat thickness information determined by insertion of a probe into the carcass, to determine a carcass classification.

U.S. Pat. No. 4,439,037 (Northeved et al., issued Mar. 27, 1984) describes an optical probe for insertion into a carcass to assess the meat-to-lard ratio of the carcass.

Ultrasound images of live animals have been analysed for the purpose of estimating the marbling or subcutaneous fat thickness of the animal. U.S. Pat. No. 4,785,817 (Stouffer, issued Nov. 22, 1988) describes an apparatus and method for using ultrasound for determining the thickness of fat on various parts of a carcass from which grading determinations can be made. Similarly, U.S. Pat. No. 5,339,815 (Liu et al., issued Aug. 23, 1994), addressing ultrasonic imaging of beef cattle, teaches associating the autocorrelation property of ultrasound speckle noise with beef marbling score.

International Application WO 93/21597 (Benn et al., International Filing Date—Apr. 13, 1993) teaches one method for tracing the outline of a digital image of a rib eye muscle of a carcass in which links are defined between pairs of concavities in the rib eye outline in order to excise image sections external to the rib eye.

International Application WO 92/00523 (Newman, International Filing Date—Jun. 24, 1991) describes a method of grading carcasses after slaughter involving the steps of checking for the presence of a carcass in the field of view of a camera, checking that the carcass is properly oriented with respect to the camera, acquiring images of the carcass from a plurality of viewpoints, determining a plurality of dimensions of the carcass from the images and comparing the dimensions with stored values to determine a grade for the carcass. However, there is no description of how the dimensions of the carcass might be determined or how they could be related to the carcass grade.

International Application WO 91/14180 (Benn, International Filing Date Mar. 14, 1991) describes a method for evaluating carcasses by object image processing involving the steps of recording an image of a background, recording a second image of a carcass positioned in front of the background, analysing the first and second images to differentiate the carcass from the background by subtracting the first or second image from the other for each colour component to provide a series of component difference images which are recombined to provide an absolute difference image. The application states that anatomical points can be identified on the carcass by comparing the area of the carcass profile with a series of reference profiles, and matching the anatomical points of the images having the most similar area. It is stated that quantitative dimensional measurements can be taken from anatomical points to predict composition, but there is no description of how to make the quantitative measurements, which ones might be useful, or how to make a prediction based on the measurements.

In concluding, the systems described above do not permit continuous grade or yield calculations of carcasses to be made during the slaughtering procedure. Techniques are needed to reliably take accurate and reproducible measurements of carcass dimensions without manual identification of anatomical features of the carcass and to develop yield predictions based on these carcass measurements. This requires the identification of specific definite and reproducible carcass measurements that are closely correlated to the grade or yield parameter of interest. Refined rib eye tracing techniques are also required to obtain accurate rib eye measurements which may also be used in grade and yield determinations.

SUMMARY OF THE INVENTION

The inventors have developed a rapid and accurate process and apparatus for the on-line grading of carcasses being processed in a slaughtering facility. Visible spectrum video images of skinned carcass halves suspended from a dressing rail are obtained, digitized and stored in computer memory for image processing and analysis. The outline of the carcass image is traced and anatomical features of the carcass, such as the tail, are identified as indentations or protrusions in the carcass image outline by methods disclosed herein. While a lateral view of a carcass half is preferably used, other carcass views, or images of intact carcasses may be useful.

Once one or more anatomical features have been identified on the carcass outline, additional reference points can be located on the carcass image at pre-determined positions relative to the original anatomical features first identified. For example, an additional reference point might be located a specific percentage of the length along a line joining two anatomical features. In this manner, by locating a small number of anatomical features of the carcass, it is possible to rapidly, accurately and reproducibly identify any number of additional reference points on or within the carcass image outline. These additional reference points may reflect anatomical features of the carcass that are not readily identified as clear landmarks on the carcass image outline. Alternatively, the additional reference points may be arbitrarily assigned points that are useful for providing a multitude of defined, reproducible locations from which various one- or two-dimensional measurements can be made.

Using the various reference points identified, a plurality of carcass image measurements are made. These may include, among other things, linear distances between reference points, areas bounded by reference points, angular measurements between selected sets of three reference points, and curvature measurements along the carcass image outline. Using known statistical techniques such as stepwise regression, predictive equations have been developed wherein a selected carcass grading parameter is included as a dependent variable, and various carcass image measurements are included as independent variables.

In the exemplified case, relating to beef carcasses, particularly useful independent variables have proven to be the shortest distance from each of a plurality of reference points along the carcass image outline to a mid-line established parallel to the long-axis of the carcass image outline which divides the image into roughly dorsal and ventral portions, the width of the carcass image outline, and the areas of regions of the carcass image which have boundaries approximating those of standard carcass primal cuts. Primal cuts are the gross sections into which a carcass is first cut during the butchering process and from which the remaining cuts made during the fabrication process depend. The inventors have developed a method for rapidly approximating the standard primal cuts on the carcass image involving dividing the carcass image into sections bounded by lines joining pre-determined reference points on and within the carcass image outline. The area of certain primal cuts, and the ratio of the area of these primal cuts to the total carcass image area have proven to be particularly useful as independent variables in predictive equations to predict such things as the saleable yield of the carcass.

Stepwise regression techniques are used to determine the degree of linear association between each of the measurements obtained from the carcass image and the selected grading parameter of the carcass, and to determine the best model for predicting the value of the selected grading parameter of the carcass in which a plurality of carcass image measurements form independent variables. Once a predictive equation has been developed, the system can be used to take carcass image measurements from additional carcasses, and the predictive equation can be solved for those measurements, to provide an output of the value of the selected grading parameter of the carcass. Though predictive equations can be developed to predict the value of a wide variety of carcass grading parameters, a particularly useful application of the invention is the prediction of saleable yield of a carcass. The definition of "saleable yield" will vary among different markets for butchered meat products. Generally, it reflects the sum of the weight of initial carcass cuts at a defined fat cover level plus the weight of trim piles at various lean percentages. In the Examples herein, "saleable yield" was defined as the total weight of all cuts with ¼" (6.25 mm) fat cover, wherein all cuts are derived from the eight primal cuts of hip, sirloin, loin, rib, chuck, flank, plate, and brisket, plus trim piles of 50%, 75% and 85% lean.

Broadly stated then, in one preferred embodiment, the invention provides a process for determining a grading parameter of a carcass, comprising the steps of:

(a) obtaining an image of a view of the carcass, the image being composed of an array of pixels providing data representative of information at the corresponding part of the image;

(b) tracing the outline of the image to produce a carcass image outline;

(c) locating a plurality of first reference points on the carcass image outline, the first reference points representing anatomical features of the carcass, the anatomical features being identified as protrusions or indentations in the carcass image outline;

(d) locating at least one second reference point on or within the carcass image outline, the second reference points being located at pre-determined positions relative to the first reference points;

(e) dividing the carcass image into a plurality of sections, the boundaries of each section being determined as a function of the position of the first and second reference points, and determining the area of each section;

(f) providing a grading parameter predictive equation wherein the grading parameter is included as a dependent variable, and at least one area of a section determined in step (e) is included as an independent variable; and, (g) solving the grading parameter predictive equation to provide a value for the grading parameter of the carcass.

The invention extends to analysis of the rib eye of the carcass. During the slaughtering process, the carcass is cut transversely between the ribs, generally between the 12th and 13th ribs. The cut does not extend clear through the carcass so that the carcass is left intact, in one piece, hanging from the dressing rail. The weight of the carcass opens the cut, allowing observation of a cross-section of the longissimus dorsi muscle, which, in beef cattle, is typically called the "rib eyed", and in hogs is called the "loin eye". As used herein and in the claims, the term "rib eye" includes the longissimus dorsi muscle of cattle and hogs, as typically viewed in cross-section during carcass grading. The rib eye represents the most valuable cut in red meat animals such as hogs, lambs and cattle. Grading systems throughout the world have evolved around measurements derived from the rib eye. As described previously with reference to the whole carcass, a visible spectrum video image of the rib eye of the carcass is obtained, digitized and stored in computer memory for image processing and analysis. Pixels representing muscle tissue are distinguished from pixels representing fat on the basis of a pixel colour characteristic threshold such as brightness level. Pixels representing cartilage may be identified by their low colour saturation level. The outline of the rib eye is traced, and the value for such variables as the percentage of intramuscular fat, the rib eye area, and the thickness of subcutaneous fat at various points on the rib eye outline are determined. These variables may be included as independent variables in the predictive equations for predicting carcass grading parameters based on carcass image measurements described previously.

Alternatively, the rib eye information can be used independently of measurements taken from the carcass images to develop predictive equations for predicting carcass grading parameters based only on rib eye image measurements.

Accurate grading predictions based on rib eye image measurements require accurate tracing of the rib eye outline. Muscle tissue that abuts the longissimus dorsi (rib eye) but that is not part of the longissimus dorsi must be discriminated to permit accurate rib eye measurements to be taken from the traced image. The present invention extends to novel rib eye tracing techniques wherein external image sections representing muscle tissue abutting the rib eye but not part of the rib eye are accurately identified and excised to provide superior rib eye tracing results.

As discussed above, the information derived from the traced rib eye outline may be used independently of the information derived from the carcass image to predict a carcass grading parameter such as saleable yield or quality grade (marbling). In one preferred embodiment, relating to the prediction of marbling, the invention includes acquiring images from standard quality grade reference photographs of rib eyes which are commonly used as a guide in slaughtering facilities for human graders in determining quality grade. The photographs depict rib eyes having a degree of marbling at the cut-off level for a particular grade. Traditionally, the human grader compares the rib eye under examination with the reference photographs and assigns a grade on the basis of the cut-off marbling levels between which the rib eye under examination appears to fall. In one embodiment of the present invention, the actual percentage of intramuscular fat in the sample rib eyes depicted in the reference photographs is determined by rib eye image tracing analysis. Following rib eye tracing analysis, yield grades can then be assigned to carcasses as a function of the percentage marbling calculated for the rib eye image.

BRIEF DESCRIPTION OF THE DRAWINGS

In drawings illustrating embodiments of the invention:

FIG. 2 is a side elevation of the rib eye camera connected to the CPU;

FIG. 3 is a bottom plan view of the rib eye camera, showing the positioning jig;

FIG. 4 illustrates an image of a latticed white board used for camera calibration;

FIGS. 5–7 illustrate different image searching masks useful in the present invention;

FIG. 8 illustrates division of the carcass image into a plurality of separate regions for analysis;

FIG. 9 illustrates an additional searching mask useful in the present invention;

FIGS. 20–30 illustrate successive rib eye image analysis steps of the invention;

DETAILED DESCRIPTION OF THE PREFERRED EMBODIMENT

The invention is best understood in reference to the attached figures.

I. System Overview

A. Apparatus

Figure 1:
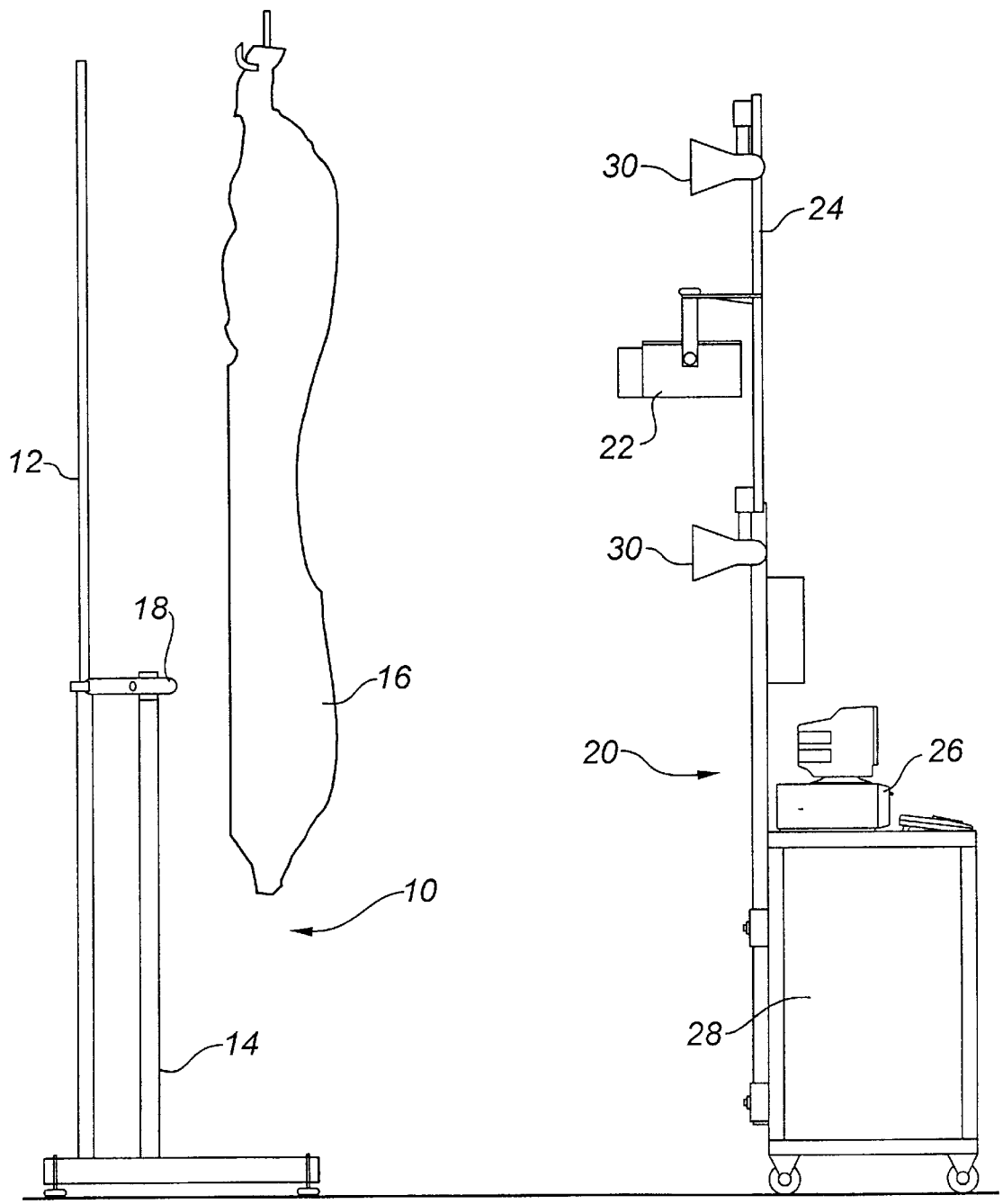
FIG. 1 is a side elevation of the carcass imaging system positioned in front of the backdrop. A carcass suspended from an overhead conveyor is positioned between the backdrop and the carcass imaging system.

Images are obtained first of intact beef carcass halves hanging from a dressing rail. Intact carcass images may be taken within a few hours after slaughter, when the carcass is still near body temperature, or after the carcass has been chilled prior to further processing. The timing of making the intact carcass image is not essential. As shown in FIG. 1, a backdrop 10 made up of four collapsible background panels 12 mounted on a stainless steel frame 14 and supported on casters, can be positioned about two feet (60 cm) behind the carcass 16 carried on an overhead conveyor and ten feet (3 m) in front of a CCD camera. One of the panels 12 may be reversible, having a grid design on one side and a black surface on the other. The grid is useful for calibrating a camera. Five squares in the centre column of the grid, one coloured each of black, white, red, green and blue are provided for colour calibration. The background panels 12 provide a non-reflective blue (or other colour having a hue that is distinct from the hue of any significant portion of the carcass—blue or green therefore being preferred) background behind the carcasses 16 to facilitate tracing of the outline of the carcass 16. One or more glide bars 18 attached to the frame 14 and oriented parallel to the direction of carcass 16 travel, maintain the carcass 16 at a desired distance from the panels 12, in a plane perpendicular to the camera. When a carcass 16 moves to the centre of the backdrop 10, the system triggers a camera to capture its image.

The carcass imaging system 20 includes a CCD camera 22, two flood light assemblies 24 (only one is visible in FIG. 1) and CPU 26 are mounted on a mobile base 28. The hot carcass imaging system 20 is positioned at a desired distance in front of the carcass 16 travelling along the overhead conveyor and the backdrop 10 is positioned behind the carcass 16 in line with the hot carcass imaging system 20.

The flood light assemblies 24 are directed toward the backdrop 10. Each flood light assembly 24 includes two 110V 250 W halogen lamps 30, mounted in waterproof stainless steel housings. Preferably, the lamps 30 are positioned about five feet (1.5 m) in front of the backdrop 10. While flood light assemblies 24 are shown mounted on mobile base 28, they may alternatively be either mounted on the ceiling or free standing. The entire hot carcass imaging system 20 is preferably collapsible for easy moving and storage.

CCD camera 22 may be a Panasonic 3-CCD industrial colour camera (model GP-US502) mounted in a stainless steel housing and powered by a 12V DC supply. The RGB video signal generated by the camera 22 is fed to a Matrox image digitizing board (Matrox Electronic Systems Ltd., Dorval, Quebec, Canada) (not shown) in the CPU 26. The CPU is contained in a stainless steel box (not shown) to conform with slaughter facility sanitary regulations. The CPU 26 may be a Pentium 150 MHz computer running software under Microsoft Windows 95 operating systems. The digitizing board grabs an image of a carcass 16 when the carcass 16 moves into position in front of the backdrop 10. The outline of the carcass 16 is traced, certain anatomical points are determined, a series of linear, 2-dimensional and angular measurements are made, and the results and image are saved.

Images of the rib eye area of the carcass 16 are generally taken after the carcass 16 has been chilled for 24 hours. While rib eye images could be taken from hot carcasses, it would be more difficult to distinguish intramuscular fat from lean muscle tissue. As shown in FIGS. 2 and 3, the rib eye image system 32 includes a hand held rib eye camera 34 and a CPU 36. Rib eye images are taken of a partial cross section of the carcass 16 between the 12th and 13th ribs. This is the rib eye muscle site normally graded by government inspectors. Therefore, the camera 34 should be portable so that it can be placed into the V-shaped notch cut between the 12th and 13th ribs of the carcass. The hand held camera 34 may be a Panasonic 3-CCD camera, similar to CCD camera 24, mounted inside a stainless steel housing 38. Two EXN 12 V, 50 W low voltage display lamps 40 are mounted on each side of the camera 34. A toggle switch 42 on the camera handle 44 is connected to an input/output board on the CPU 36, which in turn informs the CPU 36 to grab an image.

The hand-held camera 34 is mounted on a jig 46 having a positioning tab 48 which correctly positions the camera 34 relative to the rib eye muscle area of the carcass 16. Alternatively, a light weight remote camera head having a small camera and lens unit connected to a remote control unit (not shown), may be used. The camera head could be mounted directly on a small light weight jig similar to jig 46 for easy manipulation.

CPU 36 may be a Pentium 150 MHZ computer mounted in a stainless steel housing 38. The CPU 16 runs software under Microsoft Windows 95 operating systems. The software grabs an image of a rib eye. It traces the outline of the rib eye muscle, calculates the rib eye muscle area and the length and width of the rib eye, measures the thickness of subcutaneous fat, the colour of the muscle and the percentage of intramuscular fat. The software then saves the results and image.

The following additional computer hardware and software may be utilized with the hot carcass imaging system 20 and rib eye muscle imaging system 32 described above:

- A Matrox MGA Millenium video display adapter (Matrox Electronic Systems, Ltd.) for the display of live (30 fps in 32 bit colour) video on-screen;
- A Matrox Meteor image digitizing board (Matrox Electronic Systems, Ltd.) to capture images;
- A PC-TIO-10 Input/Output board (National Instruments Corporation, Austin, Tex.) used to accept an external trigger to signal the software to acquire an image from the video digitizer;
- A FASTCOM/IG232 communication port (Industrial Computer Source, San Diego, Calif.) used for serial communication with packing plant communications systems;
- A Minolta Spectrophotometer for initial program calibration and testing;
- A JVC 3-chip RGB camera (model GP-U5502) used as a video input source;
- A Microsoft Windows 95 operating system (Microsoft, Redmond, Wash.) under which development occurred;
- Microsoft Visual C++ V4.0 used as the main development environment including C++ language, debugger, interface builder, and Microsoft Foundation Classes;
- A Matrox Imaging Library (MIL) Lite (Matrox Electronic Systems, Ltd.) basic frame grabber interface for acquiring RGB images from a video source;
- An NI-DAQ Function library I/O board interface (National Instruments Corporation), allowing software to be triggered by an external button attached to a hardware interface on a computer; and,
- JPEG library version 6 (Independent JPEG Group) program code for reading and writing JPEG formatted images to secondary storage devices.

B. Image Processing

The system comprises two subsystems, a carcass image processing subsystem and a rib eye image processing subsystem. The carcass measurements may be taken from the hot carcass immediately during the slaughtering procedure or after some period of chilling. Rib eye measurements are typically taken after 24 hours of chilling.

1. Carcass Image Processing

The carcass imaging system 20 is used to acquire a visible spectrum image of an entire half beef carcass moving along a dressing rail during the slaughtering procedure. The carcass has been bisected into two symmetrical halves along its dorsal axis.

Two carcass orientations (carcass side viewed) are possible for each of the left and right halves of the carcass, resulting in four possible views: (a) bone-side left; (b) bone-side right; (c) skin-side left; and, (d) skin-side right. The left skin-side of the carcass is used in the Canadian beef grading system. The other views are not used in the Canadian system.

As the carcass halves come down the line, either the bone-side or the skin-side may face the camera. An operator standing upstream from the carcass imaging system 20 manually flips the carcass halves into the skin-side orientation. The carcass imaging system 20 differentiates between the left and right carcass halves, and retains images of the selected carcass half for analysis.

Various linear, two-dimensional and curvature measurements of the carcass are made, as will be discussed in detail herein. A total of approximately 400 measurements are made. Prediction equations can be developed from these measurements to (i) predict carcass conformation, (ii) sort carcasses into size groups and (iii) provide precise coordinates for automated fabrication of primal cuts by robotic machinery.

2. Rib Eye Image Processing

After 24 hours of chilling, a cut is made between the 12th and 13th ribs of the carcass to expose the longissimus dorsi muscle, also called the rib eye. Manual observation of a cross section of the rib eye is a conventional carcass grading technique. The weight of the carcass opens the cut so that the hand held camera 34 may be inserted in the resulting notch and an image taken. There are two principal reasons that the rib eye is examined for meat grading purposes. First, rib eye grading measurements are known to correlate closely with the grade of the rest of the carcass. Secondly, the rib eye is the most expensive cut of meat in the carcass and is therefore of the greatest importance for grading purposes.

Generally, the rib eye area analysis involves the following steps:

a. The bottom edge of the rib eye area is detected.

The bottom edge of the rib eye muscle area is defined by a fat/air boundary. It represents the outer edge of a cross-section of the carcass. This step is taken to determine if there is anything in the image that would interfere with the image thresholding step. This step is optional.

b. Determine threshold brightness levels over the whole carcass image area to distinguish lean tissue from fat.

The background is presumed to be all areas of the image below the bottom edge of the rib eye area determined in step a. All pixels below this edge are set to black.

c. Trace the boundary of the rib eye muscle.

d. Determine the area and the percentage marbling inside the rib eye muscle boundary.

e. Determine the longest axis of the rib eye muscle area.

f. Determine the greatest width of the rib eye muscle area, perpendicular to the longest axis.

g. Determine the approximate location of the subcutaneous fat layer. The subcutaneous fat is found in the area between the external carcass boundary and the edge of the rib eye muscle.

h. Measure the thickness of the subcutaneous fat by dividing the long axis of the rib eye muscle area into four equal quadrants and measuring the thickness of the fat at the boundary between each of the quadrants.

II. Colour Analysis of Meat Tissues

Carcass analysis in the present invention involves three principal types of tissue, meat (muscle), fat and gristle (cartilage). Each of these tissue types has distinguishing colour characteristics.

The colour of light is a function of its electromagnetic wavelength. Seven distinctly named colours or hues are distinguishable in the visible light spectrum, each representing a different wavelength: red, orange, yellow, green, blue, indigo and violet. Light colours, as distinguished from pigment colours, work on an additive basis. The absence of light of any colour produces black. A combination of the three primary light colours, red, green and blue, add to produce white light.

There are three dimensions or attributes of colour: hue; value, or brightness; and chroma, or saturation. "Hue" is the specific name of a colour. Hue depends on the dominant visible wavelength of a colour. The wavelength associated with the particular hue indicates that hue's position within the spectral range. The seven hues described above are considered pure hues, and cannot be separated into simpler colours. Other visible hues are combinations of several different light wavelengths (see, for instance, Wallschlaeger C., and C. Busic-Snyder, *Basic Visual Concepts and Principles for Artists, Architects, and Designers,* 1992, Wm. C. Brown Publishers). "Value", or "brightness", is the relative lightness or darkness of a colour as it would appear in a black and white photograph. The value of a colour depends on how much light the colour reflects. Colour values are referred to as "tints" or "shades". Tints are lighter in value. Shades are darker in value. "Chroma", or "saturation", refers to the amount of hue in a particular colour or the relative purity of a colour on a scale from a hue to grey. A colour that has a high chroma is said to be saturated with a monochromatic (one colour) hue. Hue, value and chroma (hue, brightness, saturation) are interrelated. For instance, at extremely high or low values, it is difficult to determine the hue or chroma of a colour as all colours will appear, respectively, very light (white) or very dark (black). Further, to the human eye, different hues may reach their maximum chroma at different values. For instance, yellow reaches its maximum chroma at a higher value (brightness) than does purple-blue. An excellent discussion of colour analysis, representation and reproduction is provided in Benson, K. Blair ed., *Television Engineering Handbook Rev. Ed.,* McGrawHill Inc., New York, 1992.

When these colour principles are applied to the tissues of an animal carcass, the differing colour characteristics of muscle tissue, fat, and cartilage can be distinguished in a digitized image of the rib eye area. Muscle tissue, having a medium value (brightness) and chroma (saturation) can be seen to have a reddish hue. Cartilage, having a low to medium value and low chroma appears an achromatic grey because the saturation or intensity of the hue (reddish) is low. Fat, having a high value, appears bright white because it is difficult to discern the hue (reddish) at very high values. Thus, cartilage can be distinguished from muscle tissue or fat on the basis of the low chroma of cartilage, and fat can be distinguished from muscle tissue or cartilage due to the high value of fat.

A number of systems may be used to define colour for computer/video applications. In the RGB system, the amount of each of red, green and blue in the colour of a pixel is defined. An RGB value may be represented in hexadecimal form (i.e. bright red FF0000, bright green 00FF00, bright blue 0000FF, black 000000, white FFFFFF). All necessary colour information can be determined from the RGB colour value. The tint or hue is determined by the relative proportions between the red, green and blue values. Thus, CC33FF will have a different hue than CC3300, the latter having a bluer hue. The brightness and saturation of the colour is also determined by the relationship between the red, green and blue values. For instance 66FF99 will have the same hue as 33CC66 (medium-green) but will be brighter.

RGB values can be converted directly into other colour systems such as HSL (hue, saturation, lightness). The HSL system is intuitively suitable for carcass image analysis purposes in that it makes direct reference to the distinguishing characteristics of hue, chroma (saturation) and value (lightness) described previously.

It has been determined that muscle tissue, fat and cartilage have the HSL colour characteristics shown in Table 1.

TABLE 1

|  | hue | saturation | lightness |
| --- | --- | --- | --- |
| muscle tissue | reddish | medium | medium |
| fat | reddish (hard to measure) | hard to measure | high |
| cartilage | reddish (hard to measure) | low | low-medium |

The colour of an object is dependent on illumination. To assess meat colour objectively, the image colour is corrected to known standard lighting conditions. The brightness of the image is first equalized to account for differences in the illumination level across the carcass surface or rib eye muscle. The image is then adjusted to standard lighting conditions.

To adjust the image for brightness, an image of a uniform 18% grey card with a known RGB colour value is recorded. The standard colour value of each pixel in the grey card image is used to adjust the colour value of each corresponding pixel in a carcass or rib eye muscle image. The RGB value of each pixel in the carcass or rib eye muscle image is adjusted to the known lighting condition as:

$$\text{Pixel}(c)^*_{ij} = \text{Pixel}(c)_{ij} \times \frac{\text{TrueGrey}(c)_{ij}}{\text{CameraGrey}(c)_{ij}}$$

where pixel$(c)^*_{ij}$ is the adjusted pixel value and pixel$(c)_{ij}$ is the pixel to be adjusted located at row i and column j and c is an R, G, or B colour component. The true grey $(c)_{ij}$ is the known grey value at standard lighting conditions and the camera grey $(c)_{ij}$ is the camera perceived value. The $(RGB)_{ij}$ at pixel$_{ij}$ becomes $(RGB)_{ij}^*$ after brightness adjustment.

The brightness corrected image is subjected to colour adjustment by a calibration matrix A as:

$$(rgb)_{ij}^{**} = (rgb)_{ij}^* \begin{bmatrix} a_{11} & a_{12} & a_{13} \\ a_{21} & a_{22} & a_{23} \\ a_{31} & a_{32} & a_{33} \end{bmatrix}$$

The calibration matrix is derived by comparing five colours (black, white, red, green and blue) to be calibrated to the same five colours under known standard lighting according to the following relationship:

$$XA=B$$

where X is a 5×3 matrix representing r,g and b values of the five colour samples, A is a 3×3 calibration matrix to be solved for, and B is a 5×3 matrix of known constants, representing the r, g, and b values of five colour samples under standard lighting. A least squares solution for the calibration matrix A is obtained as:

$$A=(X'X)^{-1}X'B$$

where X' s the transpose of matrix X and $(X'X)^{-1}$ is the inverse of matrix (X'X).

III. Hot Carcass Image Analysis

A. Camera Calibration

A latticed white board having a grid of black lines spaced at 10 cm intervals is used as a backdrop to scale the carcass image. Prior to commencing a carcass analysis session, the latticed backdrop is imaged to determine the number of pixels in the image frame (scale). A threshold value is established to distinguish the white background from the grid lines. As the board is bright white and the grid lines are dark black, that is, they are at the extremes of the brightness range, the threshold value may be arbitrarily set as the median brightness level (on an HSL colour measurement system).

As shown in FIG. 4, the digital image shows the latticed white board 100 against a background 102 of empty space. To find the area (number of pixels) in each grid square 104, the boundaries of each square 104 must be detected. Because the squares are regular geometric shapes, the boundaries of each square are defined by the regular intersections 105 of the grid lines 106. Finding the grid line intersections 105 involves searching in a regular pattern along each row and column of pixels in the image using a mask to locate a desired shape determined by the mask used. Once the grid line intersections along the grid lines defining the right edge and the bottom edge of the grid have been located, the entire grid may be extrapolated as the grid is defined by a regular geometric pattern of lines intersecting at right angles.

The intersections 105 of the grid lines 106 in the latticed background describe a number of different right angle L shapes. These could also be described as the shapes defining the four corners of a square. Masks may be defined to identify each of the possible intersection shapes. For example, if the screen shown in FIG. 4 is analysed by searching pixel by pixel, vertically upwards from right to left, along lines 108, the first intersection shape to be detected along the grid line defining the bottom edge of the grid will be a lower right corner shape. A lower right corner can be identified by a 5×5 pixel mask 110 as shown in FIG. 5, wherein the H's represent pixels of high intensity and the L's represent pixels of low intensity. The mask 110 is defined such that the sum of the brightness values in the L pixel positions is subtracted from the sum of the brightness values in the H pixel positions. The resulting difference is indicative of the fit of the mask.

Because a thresholding process is used, brightness levels will arbitrarily be reduced to two numerical designations. For instance, on a 0–255 range of brightness levels, all intermediate brightness levels may be reduced to either a value of 10 (low brightness—black line area) or 200 (high brightness—white area) depending on whether the brightness value of the pixel falls above or below a pre-determined threshold value. Thus, a lower right corner shape is detected when (sum H)−(sum L)=greatest difference for the mask 110 shown at FIG. 6. In this example, the maximum difference for the mask 110 would be (9×200)−(16×10)=1640. This difference will be achieved when the mask is located such that each H pixel is located over a bright (white background) pixel of the digital image and each L pixel in the mask is located over a dark (black grid line 106) pixel of the digital image. A better fit of the mask is indicated by a greater difference between (sum H)−(sum L).

Conversely, as shown in FIG. 7, when the mask 110 is not aligned over the lower right corner shape, the difference of (sum H)−(sum L) will be lower. For the poorly fitting mask 110 shown in FIG. 7, the difference would be ((3×200)+(6×20))−((10×200)+(6×20))=−1400. It will therefore be apparent that the mask 110 is not centred over a lower right corner shape.

The first lower right corner shape is located by searching across the image from bottom to top, one column of pixels at a time, working from right to left. Once the first lower right corner shape has been located (lower-right corner of grid), the mask 110 may be moved from right to left in the same row of pixels in the image to locate lower right corner shapes located in the same row (bottom-most horizontal grid line). By moving right to left along the X axis to determine the positions of first and second lower right corner shapes, it is possible to determine the number of pixels between the positions of the lower right corner shapes.

Other grid line 106 intersection 105 shapes such as upper right corner shapes may be detected using appropriately designed masks 110. By repeating this process along the Y axis to detect lower right corner shapes, the grid intersections on the right-most vertical grid line can be detected. By determining the number of pixels between lower right corner shapes on the right- most vertical grid line, it is possible to calculate the number of pixels in each 10 cm×10 cm square.

By calculating the number of pixels in the digital image of each 10 cm×10 cm grid square on the latticed background, the system can be calibrated to determine the actual distance represented by each pixel. This calibration becomes useful when the digital images are used for making actual measurements of carcass features.

B. Carcass Image Analysis

After the hot carcass imaging system 20 has been calibrated, the latticed background panel 12 is replaced with a backdrop panel 12 having high contrast with the carcass. Preferred panel colours are blue and green. Preferably, the panels 12 are substantially non-reflective.

The first carcass half is moved into position in front of the backdrop 10 and a digital image is recorded.

As shown in FIG. 8, analysis of the image begins by inserting a rough processing rectangle 112 around the carcass portion of the image (the image encompasses both an area in which the carcass is found, and a surrounding blue background area). The processing rectangle 112 is positioned so that it is somewhat larger than the carcass area. The processing rectangle is divided into twelve equal-sized zones 114 for image processing purposes. Brightness thresholding is conducted separately in each zone 114 to account for variation in illumination of the carcass surface. Alternatively and preferably, during camera calibration, the camera 22 may be adjusted so that the image frame is no larger than the blue background, thereby excluding any potentially interfering objects in the background.

1. Thresholding the Edge of the Carcass Image

Five equally spaced points 116 are selected along the bottom border of the lower middle zone for further analysis using a mask technique. The mask 118 used is 10 pixels long in the Y coordinate and 1 pixel wide in the X coordinate as shown in FIG. 9. The mask 118 is moved upwardly one pixel at a time in each of the columns designated by one of the five selected points 116. At each one-pixel increment, the sum of the values of the L pixels in the mask 118 is subtracted from the sum of the values of the H pixels. The values measured in the mask 118 are brightness values on an arbitrary brightness scale such as 0–255, brighter values designated as a greater number. The background/carcass border is detected when (sum H)–(sum L)=greatest value. At that point, each of the H pixels in the mask is centred over a carcass image pixel and each of the L pixels in the mask is centred over a background image pixel. The average of the low (L) pixels in the mask is determined. This represents the average brightness of the image background.

Of the five samples taken, that having the highest average background brightness is used as the reference standard. The brightness level of the background is used to set a brightness threshold to distinguish the image background (blue panels 12) from the carcass image (bright—fat covered). A small constant is added to the background (average of L pixels in mask) brightness level to provide a margin of error. Any image pixel having a brightness level higher than the threshold is presumed to be a carcass pixel.

Alternatively and preferably, the edge of the carcass image is determined on the basis of hue, rather than brightness. That is, the carcass having a reddish/yellowish hue can be readily distinguished from the backdrop which has a blue hue. To accomplish hue thresholding, the average hue of the image background (blue panels 12) is determined, preferably from an image taken of the background without a carcass present. As the background is of a substantially consistent colour, the hue can be approximated from a very small portion of the background. Turning to the carcass image, if the hue of a given image pixel differs from the average hue of the blue background by a pre-determined significant amount (for example—more than 40 degrees on the HSL colour wheel), then the pixel is presumed to represent a portion of the image containing the carcass.

2. Tracing the Edge of the Carcass Image

Once a position on the carcass border (background/carcass boundary) has been detected, the outline of the carcass is traced. As the image background (blue panels 12) is dark and the carcass outer surface is bright (fatty tissue), the tracing procedure traces the boundary between the dark and bright pixels. Working from the first carcass pixel (first pixel above threshold established in the previous step) detected at the lower right edge of the carcass border, carcass outline tracing proceeds using a basic edge chain linking algorithm to trace the inner boundary of carcass pixels in the image in a clockwise direction. Edge chain linking algorithms are well known and the basic theory and practice of such algorithms are described in Gozalez, Rafael C. et al., *Digital Image Processing*, Addison-Wesley, U.S.A., 1993. Working upwardly in each column from the lower right edge of the image frame, the first carcass pixel (bright—fat) identified using the mask 118 shown in FIG. 9 is detected. Starting with the first carcass pixel, tracing commences by moving one pixel below the first carcass pixel and tracing clockwise through the nine pixels immediately surrounding the first carcass pixel to find the next carcass pixel (next pixel having a brightness value greater than the threshold). The tracing process is then repeated until the entire carcass border has been traced. In this manner, each edge pixel in the carcass image is detected, thereby tracing the outline of the carcass image.

3. Distinguishing the Outside Left Carcass Image a. Finding the Tail

Figure 10:
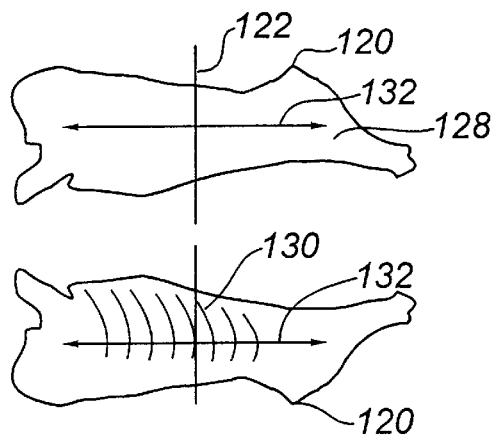
FIGS. 10–14 illustrate successive carcass image analysis steps of the invention.
Figure 11:
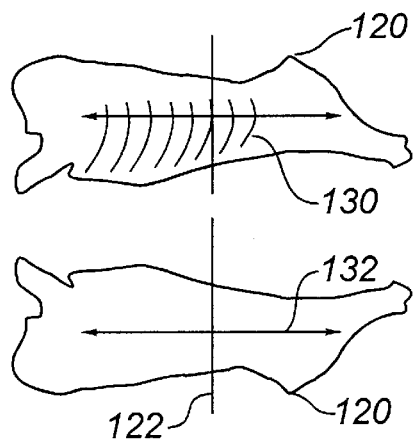

Once the carcass outline has been traced, the left and right carcass half images are distinguished. As discussed previously, in the Canadian grading system, the left side of the carcass is analysed. For use in Canada, the invention discards the images taken of the right half of the carcasses. The left and right half carcass images will appear generally as shown in FIGS. 10 and 11 respectively. Certain distinct anatomical features may be detected in each carcass image. To distinguish the right and left carcass halves, the position of the tail 120 is first detected.

To detect the position of the tail 120 in the image, the half way point in the list of X coordinates in the carcass outline (beginning from the point furthest to the lower right) is selected. The remainder of the list of X coordinates in the carcass outline is searched until the same X coordinate is found. Connecting these two X coordinates will define a line 122 bisecting the carcass into left and right halves.

Figure 12:
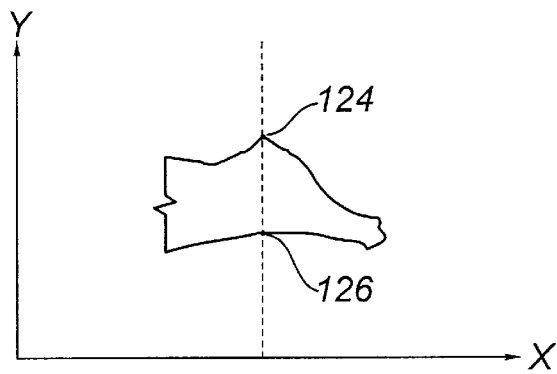

Because it is known that the tail 120 will not be found in the left half of the image, the left half of the image can be disregarded and only the right half of the image need be further analysed. As shown in FIG. 12, for each X coordinate, there will be at least two Y coordinates, one defining the upper edge 124 of the carcass, and the other defining the lower edge 126 of the carcass. The change in Y values along the line defining the carcass edge will be greatest on the edge of the carcass where the tail 120 is found.

b. Distinguishing the Bone-Side From the Skin-Side of the Carcass

Once the position of the tail 120 has been determined, the image is analysed to determine whether the image shows the bone-side or the skin-side of the carcass. As shown in FIGS. 10 and 11, the skin-side surface of the carcass is covered in a relatively homogeneous layer of fat (bright) 128. The bone-side surface of the carcass is characterized by the alternating dark and light bands 130, representing, respectively, lean tissue between the ribs and the rib bones. The ribs are not visible from the outside view of the carcass.

To identify the ribs, a horizontal (X axis) line 132 is defined a selected distance inside the carcass boundary on the tail side. The brightness value of each pixel along the horizontal line 132 is determined. Rapid significant variation in the brightness level along the horizontal line 132 indicates that the image depicts the inside surface of the carcass where the ribs are exposed. The brightness level along the outside surface of the carcass will not vary greatly as the outside surface of the carcass is covered with a relatively continuous layer of fat.

Using the information regarding the position of the tail and whether or not the ribs are in view, it is possible to determine the carcass half and orientation being viewed. The skin-side left half image is used for Canadian grading, and the skin-side right half image is used for U.S. grading. The skin-side left image is characterized by the ribs not showing, and the tail 120 appearing at the top of the image.

4. Carcass Measurements

As will be discussed in greater detail herein, a variety of measurements are made on the carcass image outline. These measurements are useful as independent variables in predictive equations for predicting various carcass grading parameters. Not all of the possible types of measurements will be used in each predictive equation. For instance, as discussed in the Examples herein, a highly accurate equation for predicting saleable yield in beef cattle was developed without using any of the oblique angle or curvature measurements discussed herein as independent variables.

The carcass measurement techniques described herein are particularly useful as they do not require any manual measurement or analysis of the carcass. Rather, certain distinctive anatomical features of the carcass may be identified by image analysis techniques. The remaining measurements may all be made as a function of the position of the anatomical features originally identified.

a. Locating Anatomical Reference Points

Figure 13:
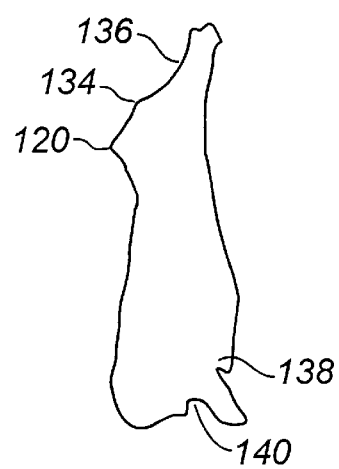

A number of anatomical carcass features can be distinguished on each carcass image outline. As shown in FIG. 13, the tail 120, lower hip 134, dorsal hind leg 136, lower armpit 138, and upper armpit 140 are characterized by readily discernible protrusions or indentations along the carcass outline and can therefore be located by image analysis techniques. To locate one of the anatomical features referenced above, analysis of the carcass image outline is restricted to a short segment of the carcass image outline within which the subject anatomical feature is known to be located.

Figure 14:
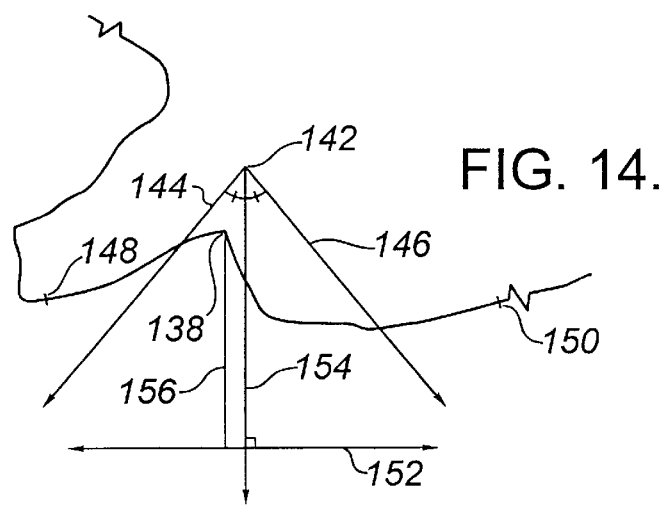

Within each selected short segment of the image outline, the anatomical feature of interest typically appears as a protrusion or indentation in the carcass image outline. As shown in FIG. 14, (a representation of the lower armpit 138) the protrusion or indentation can be estimated to be an apex 142 defined by two intersecting lines 144, 146. Although the apex 142 shown in FIG. 14 defines the position of the lower armpit 138 along the line segment bounded by 148, 150 relatively accurately, the actual position of the apex 142 and the direction of lines (vectors) 144, 146 are not critical.

A line 152 is projected perpendicular to a line 154 bisecting the angle formed by the apex 142. The furthest point along the segment of the carcass image outline under analysis from perpendicular line 152, as defined by line 156, represents the lower armpit 138. This method can be used to locate any anatomical reference point on the carcass outline that can be defined as a protrusion or indentation of the carcass image outline.

The projection of virtual lines 144, 146 and the bisection of the angle formed between lines 144, 146 is not critical. This is merely a graphical representation of one method by which to position line 152 approximately perpendicular to apex 142, so that apex 142 will be the most distant point along the line segment bounded by 148,150 from line 152.

b. Locating Other Anatomical Points

Other anatomical points, described herein as the loin, the rib, the chuck, the neck, the ventral hind leg, the flank, the 12th rib, and the brisket, can be located as proportions of the distance between certain of the previously determined anatomical reference points.

Figure 15:
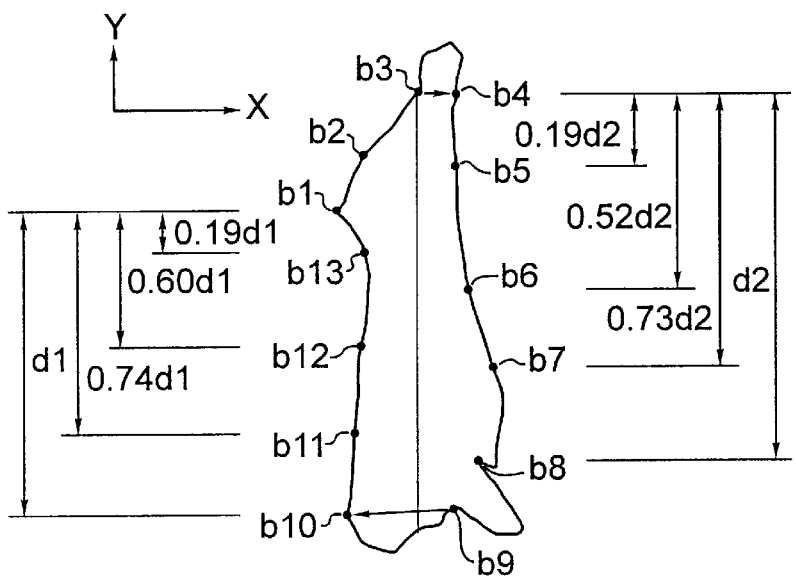
FIGS. 15–18 illustrate the identification of anatomical reference points, the estimation of primal cuts, the definition of linear measurements, and the definition of angular measurements, respectively.

As shown in FIG. 15, the distance in the X coordinate between the tail 120, located at carcass outline point b1, and the upper armpit 140, located at carcass outline point b9, is defined as $d_1$. The distance in the X coordinate between the dorsal hind leg 136, located at carcass outline point b3, and the lower armpit 138, located at carcass outline point b8, is defined as $d_2$. Anatomical points can be located as shown in FIG. 15 and Table 2.

TABLE 2

| Anatomical Point | proportion of $d_1$ | proportion of $d_2$ |
| --- | --- | --- |
| loin (b13) | 0.19 | |
| rib (b12) | 0.60 | |
| chuck (b11) | 0.74 | |
| neck (b10) | 1.00 | |
| ventral hind leg (b4) | | 0.00 |
| flank (b5) | | 0.19 |
| 12th rib (b6) | | 0.52 |
| brisket (b7) | | 0.73 | c. Defining Primal Cuts

Once the anatomical points have been determined, primal cuts may be calculated. Primal cuts are the principal cuts of meat produced during the butchering process, and which include the hip, sirloin, loin, rib, chuck, flank, plate, and brisket.

Figure 16:
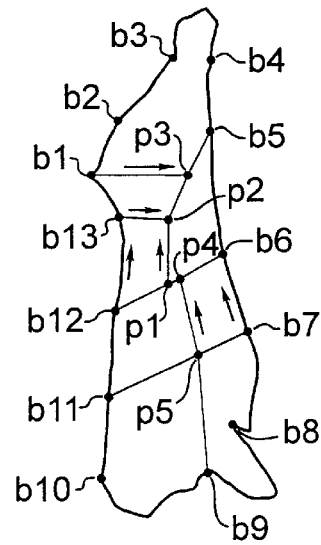

Primal cuts are shown in FIG. 16. Primal cut lines are identified by their anatomical endpoints. Point p1 is located 42% of the distance along line b12–b6.

Point p2 is located at the intersection of a line plotted upwardly from p1, parallel to line b12–b13 and a line plotted rightward from b13, parallel to the Y axis (note that the axes in FIG. 16 are reversed from their usual positions).

Point p3 is located at the intersection of line p2–b5 with a line plotted rightward from b1, parallel to the Y axis.

Point p4 is located 45% of the distance along line b12–b6.

Point p5 is located at the intersection of line b11–b7 and a line plotted downward from p4, parallel to line b6–b7.

Front primal cuts are separated from hind quarter primal cuts by line b6–b12.

The hip primal cut is bounded by the carcass edge outline and lines b1–p3 and p3–b5.

The sirloin primal cut is bounded by the carcass edge outline and lines b1–p3, p3–p2, and p2–b13.

The loin primal cut is bounded by the carcass edge outline and lines b13–p2, p2–p1, and p1–b12.

The rib primal cut is bounded by the carcass edge outline and lines b12–p4, p4–p5, and p5–b11.

The flank primal cut is bounded by the carcass edge outline and lines b5–p2, p2–p1, and p1–b6.

The plate primal cut is bounded by the carcass edge outline and lines b6–p4, p4–p5, and p5–b7.

The brisket primal cut is bounded by the carcass edge outline and lines b7–p5, and p5–b9.

The length of the carcass is recorded (length in pixels of line b3–b9) and the area of each of the eight primal cuts is determined. The sum of the areas of the eight primal cuts provides the total carcass area.

d. Linear Measurements

Linear measurements are made to divide the carcass into six linear regions, the hind leg, lower hip, upper hip, lower back, mid back and shoulder.

Figure 17:
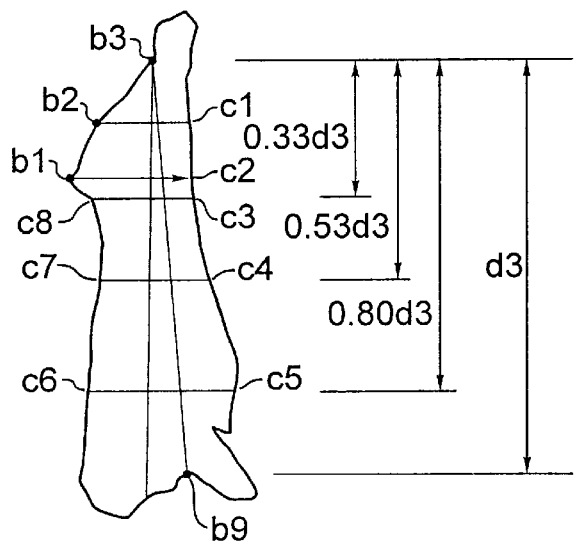

As shown in FIG. 17, line b3–b9 defines the carcass length. Carcass length line b3–b9 also divides the carcass dorsally/ventrally.

Prior to making the following measurements, the image is rotated so that line b3–b9 is parallel to the X axis (as above, axes in FIG. 17 are reversed).

Lines separate and define the linear regions. Line b2–c1, separating the hind leg region from the lower hip region, projects from b2 perpendicular to carcass length line b3–b9, to intersect the opposite side of the carcass outline at c1.

Line b1–c2, separating the lower hip from the upper hip, projects from the tail (b1) perpendicular to the carcass length line b3–b9, to intersect the opposite side of the carcass outline at c2.

Line c8–c3, separating the upper hip region from the lower back region, is made perpendicular to the carcass length line b3–b9 33% of the distance along line b3–b9.

Line c7–c4, separating the lower back region from the mid back region, is made perpendicular to the carcass length line b3–b9 53% of the distance along line b3–b9.

Line c6–c5, separating the mid back region from the shoulder region, is made perpendicular to the carcass length line b3–b9 80% of the distance along line b3–b9.

Line b3–b9, defining the carcass length, forms the basis for a series of measurements which may be useful as independent variables in equations for predicting carcass grading parameters. Each of the six linear regions (the hind leg, lower hip, upper hip, lower back, mid back and shoulder) is divided into a plurality of fine divisions, for instance 10 divisions, perpendicular to line b3–b9. The distance from line b3–b9 to the ventral or dorsal edge of the carcass image outline at each fine division may be used as an independent variable. Arithmetically dividing each of the linear regions into many small equal divisions is a convenient method for providing a large number of reproducible carcass image measurements, any of which may be useful as independent variables in predictive equations for carcass grading parameters.

e. Oblique Angle Measurements

Figure 18:
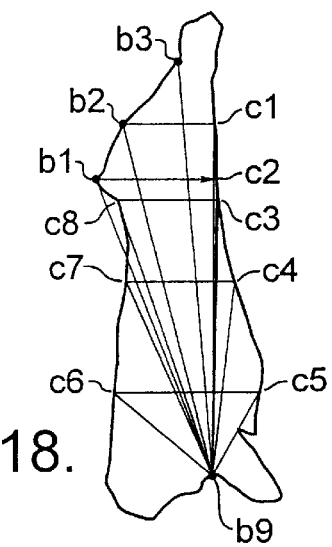

As shown in FIG. 18, the distance from b9 to each of cl, c2, c3, c4, c5, c6, c7, c8, b1 and b2 is measured. Numbering and lettering in FIG. 18 corresponds to that in FIG. 17.

Angles $\angle$c6-b9-c5, $\angle$c7-b9-c4, $\angle$c8-b9-c3, $\angle$b1-b9-c2, and $\angle$b2-b9-cl are measured.

f. Curvature Measurements

Cubic spline functions are estimated for carcass outline segments b2–b3 and b1–b13 by known methods as described in Gozalez, et al., supra.

IV. Rib Eye Muscle Image Analysis

A. Camera Calibration

1. Brightness

Using the rib eye imaging system 32, a digital image of an 18% grey card is acquired to calibrate the camera for brightness level. The image is pre-processed with a low-pass filter which allows only minor variations in brightness to pass. This eliminates variations in the brightness level across the image.

The average brightness of the uniform grey image is determined using a spectrophotometer and each image pixel is corrected for brightness as described previously. This data is utilized during carcass image analysis to compensate for lack of uniformity in the light source, and to improve the accuracy of colour measurements.

2. Colour Balance and Image Scale

Colour balance and image scale information is determined from an image acquired of a standard colour calibration sheet available from Kodak and used for colour correction as described previously. A standard colour calibration sheet has black, white, red, green and blue colour calibration squares, and a large white image area calibration square, each side being eight mm in length. The RGB values of the colour calibration squares are recorded for use in colour correction.

The image scale is determined by calculating the area of the image area calibration square on the colour calibration sheet. A row of pixels approximately half way down the image is searched from left to right. As the background of the colour calibration sheet is dark, and the image area calibration square is bright, it is assumed that any pixel along the horizontal row searched that has a brightness value below the median value on the brightness scale is a background pixel, and pixels above the median brightness value fall within the calibration square. The number of bright pixels per row is summed. This process is repeated for each row above and below the centre row of pixels in the image until the first row in both directions (up and down) is encountered which does not contain any bright pixels. When the boundary of the entire calibration square has been determined, the area of the calibration square is calculated (in number of pixels) for use in verifying the accuracy of the following image area calculation based upon a matrix solution.

During image scale determination, the top-left (TL), bottom-left (BL), and bottom-right (BR) corners of the calibration square are recorded. The length in pixels of vectors BL-TL and BL-BR is calculated and correlated to their actual lengths (8 cm). A simple matrix is solved to find kX (the X scale) and kY (the Y scale) and the results are compared to those determined in the previous step. If the results differ beyond an acceptable limit (i.e. 50 square pixels), the image calibration step is repeated. The camera is rotated slightly in each direction between each step to ensure rotation-invariant image size calibration.

B. Rib Eye Muscle Image Acquisition

After 24 hours of chilling, a cut is made between the 12th and 13th ribs of the carcass. The weight of the carcass opens the cut so that the rib eye camera 34 may be inserted in the resulting notch and an image taken.

The rib eye imaging system 32 is used to take a digital image of the rib eye area. As discussed previously, the rib eye is the common name for the longissimus dorsi muscle. There are two principal reasons that the rib eye muscle is examined for meat grading purposes. First, rib eye muscle grading measurements are known to correlate closely with the grade of the rest of the carcass. Secondly, the rib eye is the most expensive cut of meat in the carcass and is therefore of the greatest importance for grading purposes.

The digital image of the rib eye muscle area is corrected for any deviation in brightness by adding each pixel brightness deviation as calculated previously for each pixel in the uniform grey brightness calibration image to the brightness value of each pixel in the rib eye muscle area image.

C. Pre-processing of Rib Eye Muscle Image

1. Tracing of Outer Fat Edge

Figure 19:
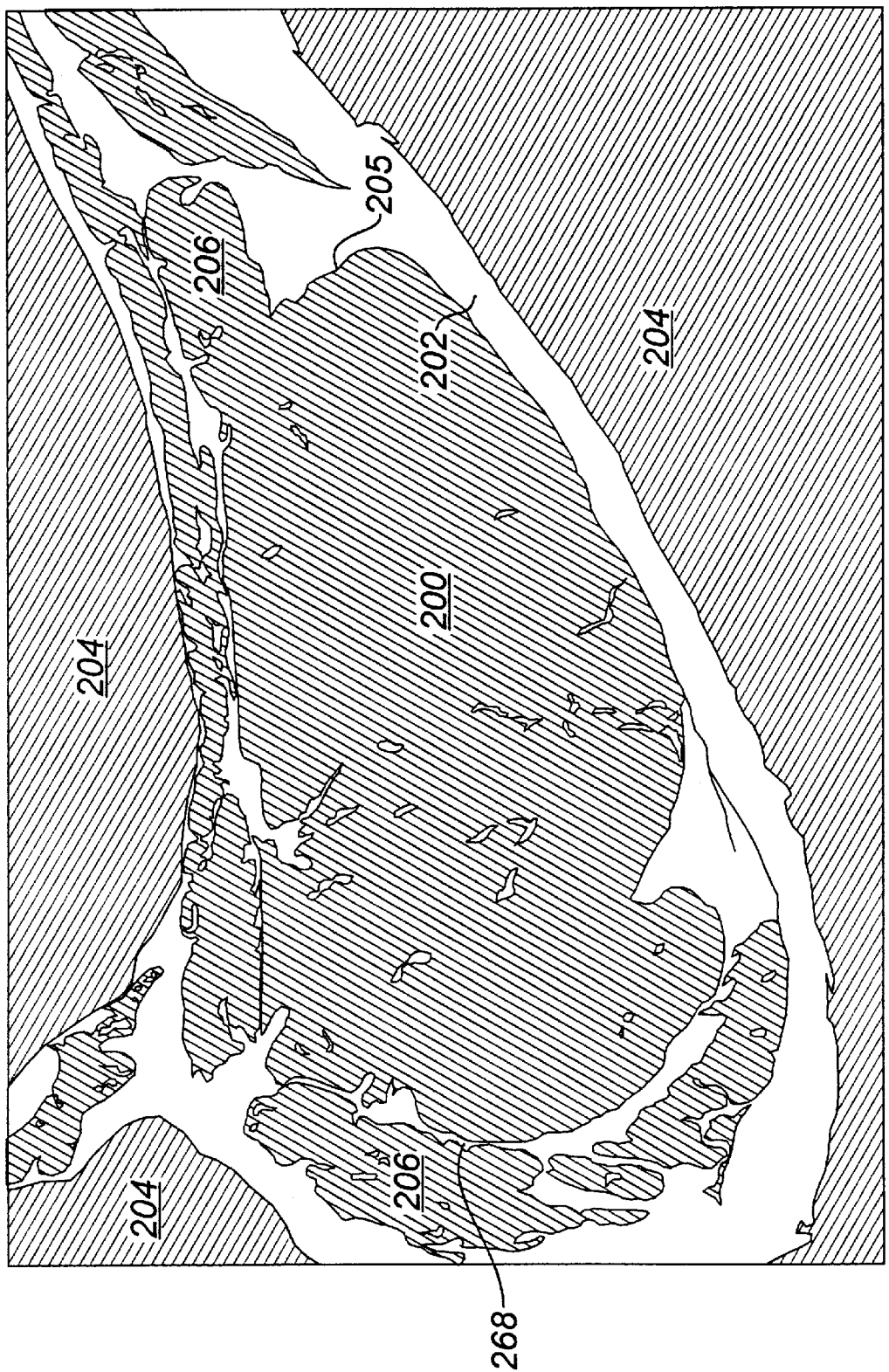
FIG. 19 shows the general appearance of a rib eye in an unprocessed digital image.

The rib eye muscle image appears generally as shown in FIG. 19. The rib eye (longissimus dorsi muscle) 200 appears as a generally elliptical dark region in the centre of the image. Subcutaneous fat 202 appears as a bright band below the rib eye muscle 200. The background 204 is the open space surrounding the hanging carcass and appears dark. Muscle tissue 206 which abuts but is not part of the rib eye 200 may be present.

Figure 20:
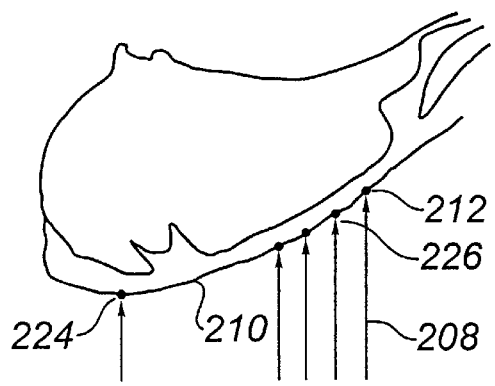

As shown in FIG. 20, the image is searched from bottom to top along a plurality of narrowly spaced columns of pixels 208, spaced about 5 mm apart (actual distance on rib eye muscle) to locate distinct rises in pixel brightness. In this step, the image is analysed in 5-pixel increments in order to rapidly approximate the outer fat edge 210 of the image. Each distinct rise in pixel brightness in a column of pixels 208 identifies a point 212 located approximately along the outer fat edge.

Points 212 are joined along a minimal energy path. A minimal energy path has little internal energy. That is, it is as straight a line as possible. A straight line has no internal energy whereas a zig-zag line has high internal energy. This path defines the approximated outer fat edge 210. If the approximated outer fat edge 210 does not span the entire image horizontally, it is extended horizontally as a straight line left-right to the image borders.

Figure 21:
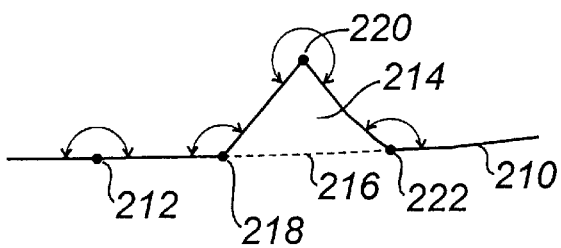

The outer fat edge 210 of the carcass may be damaged by small cuts or nicks. These will appear as irregularities or indentations in the approximated outer fat edge. A smoothing process is therefore used to even-out the approximated outer fat edge and disregard small irregularities. As shown in FIG. 21, damage to the outer fat edge 210 will likely appear as a small indentation 214 in the approximated outer fat edge. Most indentations can be represented as three "turns" in approximated line 216. Normally, the approximated line forms a 180° angle around a point 212. At an indentation 214, line 216 makes at least three turns 218, 220, 222. A turn is recognized to occur when the angle of the approximated line 210 around a point 212 differs substantially from 180°. The first and last turns over a small area indicate the beginning and end of a deviation in the approximated outer fat edge line 210. The points 212 at the first turn 218 and last turn 222 are joined to eliminate the indentation 214. Points within the indentation are transposed onto the new smoothed line.

All pixels below the smoothed approximated outer fat edge line 210 are set to a minimum brightness level (black) in order to avoid extraneous interference with image processing by any objects appearing in the background of the image.

2. Differentiating Left and Right Carcass Side Images

Any right-side rib eye muscle images will be flipped horizontally and processed like left side images. All algorithms may be designed to process the left-side rib eye muscle images, if the system is designed for Canadian grading standards.

As shown in FIG. 20, the bottom edge of the rib eye muscle tapers upwardly on one side. On the right half of the carcass, the rib-eye will taper upwardly on the left. On the left half of the carcass, the rib-eye will taper upwardly on the right.

The Y coordinate value of two points 224, 226 along the approximated outer fat edge line 210, spaced approximately 20% inside the left and right image borders is measured. If the left-most point 224 is closer to the top of the image frame than is the right-most point 226, the image represents the right side of the carcass. If the right-most point 226 is closer to the top of the image frame than is the left-most point 224, the image represents the left side of the carcass.

3. Thresholding of the Image

The entire image is thresholded for brightness to distinguish pixels representing muscle tissue (medium brightness or value) from pixels representing fat (high brightness or value) and thresholded for saturation to distinguish pixels representing muscle tissue (medium saturation) from pixels representing cartilage (low saturation).

a. Increasing Image Contrast

Each pixel in the rib eye muscle image is re-mapped onto a high contrast image ("IMap"). The brightness level of each pixel in the IMap is calculated by the formula:

$$IMap(i) = 255(1.0 - (Y(i)/255))^{2/3}$$

where $Y(i)$ is the brightness component (0:255) of the pixel value at position "i" of the image. This function enhances or exaggerates this brightness difference between muscle tissue pixels and fat pixels, thereby increasing the image contrast. This function also results in colour reversal so muscle tissue pixels, which ordinarily appear dark and would have a low brightness number (0:255), appear bright and have a high brightness number (0:255) on the IMap, and fat pixels, which ordinarily appear bright and have a high brightness number (0:255), appear dark and have a low brightness number (0:255) on the IMap.

b. Meat Colour Brightness Thresholding

The rib eye muscle IMap image is divided into six equally sized zones prior to thresholding analysis. Colour thresholding analysis is performed separately in each zone. Any portion of the image below the outer fat edge is disregarded. This increases accuracy as the average muscle tissue colour may vary in different parts of the image.

In each section, all rib eye muscle pixels are thresholded for brightness. An arbitrary value of 55 on a scale of 0:255 is established as the cutoff value between muscle tissue and fat pixel brightness. Any pixel having a brightness value below 55 is presumed to be fat (brightness is reversed on IMap). The remaining pixels are presumed to represent either muscle tissue or cartilage.

c. Meat Colour Saturation Thresholding

In each section, the average muscle tissue pixel (pixels not determined to be fat as determined in the previous step) colour saturation is determined. A threshold saturation level is established by subtracting a constant value from the average muscle tissue colour saturation level, thereby providing a margin of error. A pixel having a saturation level below the threshold value is presumed to represent cartilage. A pixel having a saturation level over the threshold value is presumed to represent muscle tissue. For the purposes of the remaining steps, cartilage is treated as being equivalent to fat. Thus, pixels representing muscle tissue are distinguished from pixels representing any other tissue, whether fat or cartilage.

4. Reduced Scale IMap

A reduced scale IMap, denoted the "QIMap" is created in order to reduce the amount of data to be analysed in some of the following steps. The IMap is preferably scaled down at a ratio of 8:1, though other ratios may be used, to form the QIMap. Where, for instance, the scaling down ratio is 8:1, the colour information from 64 pixels in the IMap is averaged (eight in the x dimension and eight in the y dimension), and becomes the mean colour information for one pixel in the QIMap.

5. Locating the Rib Eye Muscle Within the Image by Blob Analysis

Blob analysis is used to distinguish the rib eye from extraneous muscle tissue that appears to contact the rib eye muscle, but that is not anatomically part of the rib eye muscle. In blob analysis, the muscle tissue pixels in the QIMap are grouped into four-connected objects. In four-connected object grouping, an image pixel is considered to be in the same group or blob as a pixel immediately adjacent to the left, right, top or bottom. Adjacent corner pixels are not considered to be part of the same blob. This may be contrasted with eight-connected object grouping, in which a pixel is considered to be part of the same object as a pixel occupying any of the eight surrounding pixel positions. Four-connected and eight-connected object analysis are known techniques which are described in Gozalez et al., supra.

In blob analysis of the QIMap, only those pixels having QIMap exceeding a muscle tissue brightness threshold value are considered part of a blob. The brightness threshold is established by subtracting an arbitrary constant from the average non-fat pixel IMap value for the entire image. Analysis proceeds left to right, top to bottom. However, other orderly analysis patterns may be used, such as left-right, bottom-top. Analysis proceeds until the first muscle tissue pixel in the image is detected. The pixels immediately above and to the left of the first muscle tissue pixel are examined to determine whether one or both is also a muscle tissue pixel. If the analysis proceeds from top-bottom, left-right, the pixels above and to the left of the first muscle tissue pixel located will not be muscle tissue pixels. The process continues in the same pattern until the next muscle tissue pixel is detected. Once again the pixels immediately above and to the left of the current muscle tissue pixel examined are tested to determine if one or both are also muscle tissue pixels. If yes, then the current pixel under examination is known to be part of the same blob as the muscle tissue pixel immediately above and/or to the left. Where a pixel is determined to be part of a first blob, and is subsequently determined to also be connected to a second blob, it is concluded that what originally appeared to be two blobs actually form a single blob.

The largest blob detected during blob analysis is indicative of the position and size of the rib eye muscle.

6. Estimating the Position of the Rib Eye Muscle in the Image

A small area within the rib eye image in which the rib eye muscle itself is actually located is demarcated by defining a processing area denoting the rib eye box around the rib eye muscle. The accuracy of colour discrimination of different tissues is increased as, to the greatest extent possible, extraneous tissue around the rib eye muscle area is excluded from analysis. To define the rib eye box, the approximate position of each of the top, bottom, left and right edges of the rib eye muscle are determined.

a. Locating the Right Edge of the Rib Eye Muscle

Figure 22:
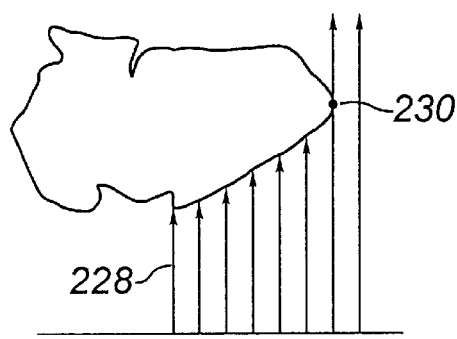

Starting at the centre of the bottom edge of the QIMap and working to the right, each column of pixels is searched from bottom to top, stopping when the first muscle tissue pixel is located. As shown in FIG. 22, the length of the columns of non-muscle tissue pixels 228 will become substantially longer when the right edge 230 of the rib eye muscle is reached. Therefore, when the length of the column of non-muscle tissue pixels becomes substantially longer, it is known that the position of the right edge of the rib eye muscle has been detected. This column is defined as the right side of the rib eye box.

b. Locating the Bottom Edge of the Rib Eye Muscle

Figure 23:

Starting at the centre of the right edge of the QIMap and working toward the bottom edge, each row of pixels is searched from right to left, stopping when the first muscle tissue pixel is located. As shown in FIG. 23, the length of the rows 232 of non-muscle tissue pixels will become substantially longer when the bottom edge of the rib eye muscle is reached. Therefore, when the length of the row of non-muscle tissue pixels becomes substantially longer, it is known that the position of the bottom edge of the rib eye muscle has been detected. This row 234 defines the bottom side of the rib eye box.

c. Locating the Top Edge of the Rib Eye Muscle

Figure 24:
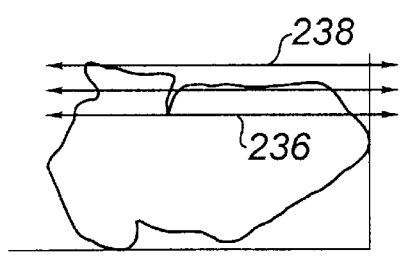

As shown in FIG. 24, a row of pixels 236 in the QIMap is selected approximately 5 cm (actual measurement on rib eye muscle) above the bottom side of the rib eye box. The total number of muscle tissue pixels on the row up to the column where the right edge of the rib eye muscle has been located is tabulated. Moving upwardly towards the top of the image, one row of pixels at a time, the tabulation of the total number of muscle tissue pixels on each row continues until the sum of the lengths of the pixels on the row is less than 2.5 cm, based on the image size calibration. The first row 238 detected where the sum of the lengths of the pixels is less than 2.5 cm is presumed to be the top edge of the rib eye muscle and defines the top side of the rib eye box. By summing the total number of muscle tissue pixels in a row, rather than using only continuous runs of muscle tissue pixels, discontinuities in the rib eye muscle edge are disregarded for the purpose of this approximation of the location of the top edge of the rib eye muscle.

d. Locating the Left Edge of the Rib Eye Muscle

Figure 25:
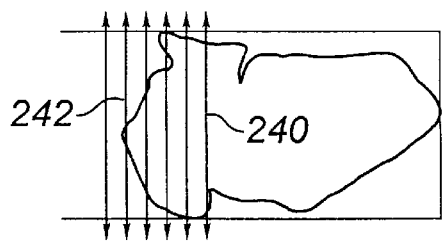

As shown in FIG. 25, a column of pixels 240 on the QIMap located approximately 13 cm (actual rib eye muscle measurement) left of the right side of the rib eye box is selected and the total length of the number of muscle tissue pixels in the portion of the column bounded by the top and bottom sides of the rib eye box is determined. This measurement is made in each column, working to the left, until the total length represented by the muscle tissue pixels in the column is less than 1.5 cm. This column 242 indicates the position of the left edge of the rib eye muscle and is defined as the left side of the rib eye box.

7. Secondary Thresholding to Improve Muscle Tissue/Fat Discrimination

The rib eye box defined on the QIMap is projected onto the IMap and the pixels within the rib eye box which were not concluded in step IV(C)(3) to be fat or cartilage are re-thresholded in each of the six zones calculated in step IV(C)(3). As many pixels clearly representing cartilage and fat were already identified by saturation and brightness thresholding in step IV(C)(3), and the area outside the rib eye box can be disregarded, colour brightness thresholding of the rib eye muscle can be accomplished with greater sensitivity. This allows fat having a slightly dark or reddish tinge to be distinguished from lean muscle tissue.

8. Rib Eye Muscle Edge Tracing

Rib eye muscle edge tracing is conducted on the IMap. The rib eye box is divided into upper and lower halves and three vertical columns to form six equal zones. Tracing starts in the column of pixels at the centre of the bottom side of the rib eye box. Working from bottom to top, the column of pixels is examined until the first muscle tissue pixel is located. This is presumed to be a pixel on the edge of the rib eye muscle.

The rib eye muscle is traced using an eight-connected edge tracing technique as discussed previously, now tracing in a counter-clockwise direction. Approximately the last ten edge pixel positions are cached.

Tracing around the rib eye muscle continues until the first rib eye muscle edge pixel is again reached. If the area defined by the rib eye muscle edge is too small, that is, below an arbitrary cut-off value, the trace is discarded and edge tracing is repeated from a new starting point upwards from the original first edge pixel and above the traced area rejected. This avoids errors resulting from commencing tracing from a muscle tissue pixel that is not on the rib eye muscle edge.

a. Identifying Extraneous Muscle Tissue Attached to the Rib Eye Muscle

Extraneous muscle tissue that is not part of the rib eye muscle may nevertheless appear to be attached to the rib eye muscle on the basis of blob analysis. The extraneous muscle tissue must be identified and removed during rib eye muscle tracing. Removal of extraneous muscle tissue involves tracing inside the extraneous muscle, thereby cutting it off from the rib eye muscle. As used herein, "cutting" or making a "cut" means the process of excluding extraneous tissue from the rib eye muscle by estimating the actual rib eye muscle edge and tracing inside the extraneous muscle tissue.

As shown in FIG. 19, the rib eye muscle edge 205, while generally relatively straight, typically turns sharply outwardly where extraneous muscle tissue 206 is attached. Such sections of muscle can therefore be identified by sharp turns in the rib eye muscle edge.

Figure 26:
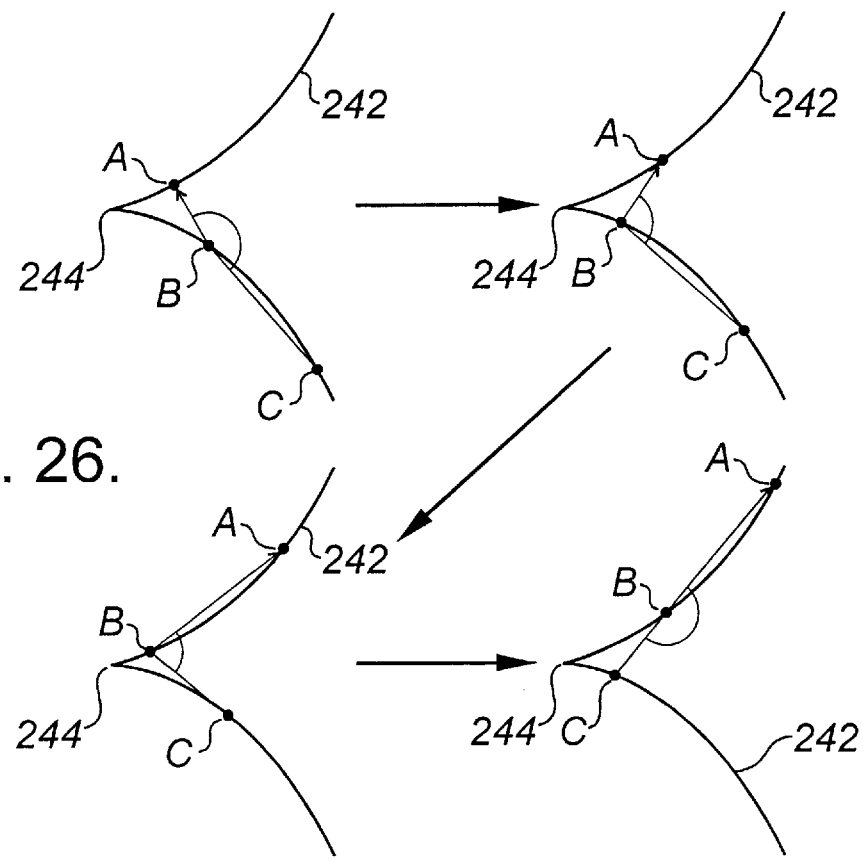

As shown in FIG. 26, during rib eye muscle tracing, a group of 10 pixels is examined at a time, the 10 pixel group moving incrementally along the traced edge 242. The angle ∠ABC is measured at each incremental step. It is known that the traced rib eye muscle edge is turning sharply when ∠ABC falls below a selected acute angle such as 45°. As shown in FIG. 26, ∠ABC will only be less than 45° when point B is near the vertex 244 of the turn. A turn is defined as an area along the traced rib eye muscle edge from the point along the edge (position of B) where ∠ABC first falls below 45° (or some other prescribed angle) and the point along the edge where ∠ABC first again becomes greater than 45°.

Figure 27:
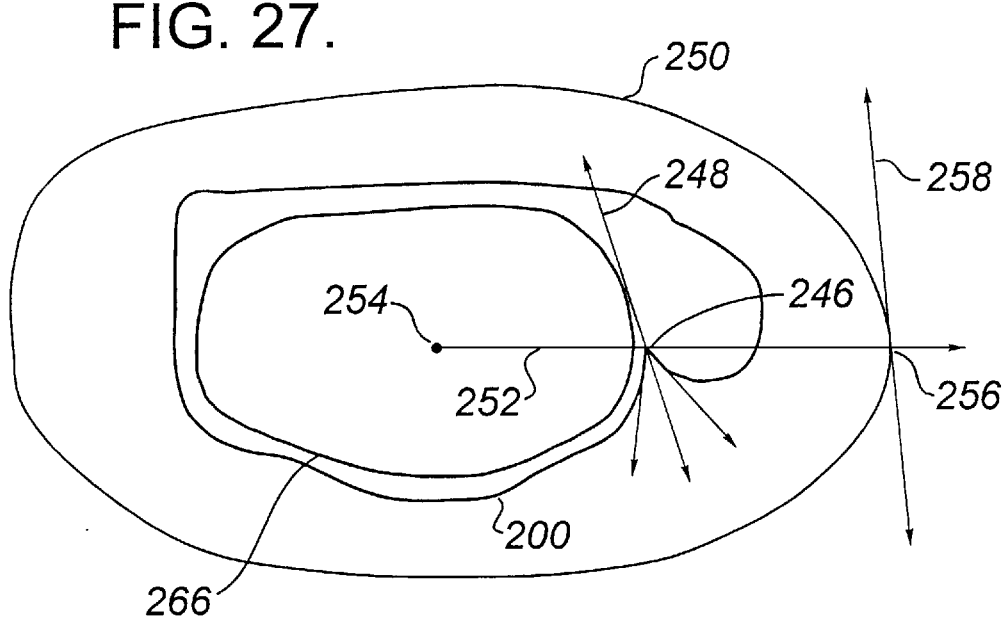

FIG. 27 is a symbolic representation of the outline of the rib eye 200, showing a sharp turn 246. When a sharp turn 246 has been identified, a line 248 is plotted, bisecting the angle formed by the turn 246.

A roughly elliptical or egg-shaped FIG. 250 is plotted, surrounding the rib eye muscle 200. The ellipse 250 roughly approximates the general shape of the rib eye muscle and fits closely within the rib eye box, contacting the rib eye box on each of its four sides. A line 252 is plotted from the centre 254 of the ellipse through the vertex of the turn to intersect a point 256 on the ellipse. A line 258 is plotted through the point on the ellipse tangent to the ellipse. Lines 248 and 258 are compared. If they are roughly parallel, the turn 246 is further considered as a site for cutting. The turn 246 is given further consideration for cutting because the roughly parallel direction of lines 248 and 258 suggest that the proposed cut (near line 248) would follow the predicted rib eye muscle edge, rather than cutting in towards the centre of the rib eye muscle along a path that would be atypical of a rib eye muscle outline. If lines 248 and 258 are not roughly parallel, the turn 246 is rejected as a potential cutting site, and tracing continues because the proposed cut would likely not follow the predicted rib eye muscle edge, but would be directed toward the centre of the rib eye muscle.

b. Determining the Path of a Cut

As shown in FIG. 28, if cutting at a sharp turn 246 identified in the previous step has not been rejected, a series of lines 260 radiating from the vertex of the turn 246 are plotted approximately 60° to either side of the line bisecting the turn. The sum of the brightness values along each line 260 is recorded. Recording stops when the line reaches a significant body of fat (i.e. 4 or more consecutive pixels). This may represent fat at the edge of the rib eye muscle 262 or intramuscular fat 264. As colours are reversed on the IMap, high brightness values represent muscle tissue. A line having a high brightness sum is either a long line through muscle tissue, or it is interrupted by few fat pixels. A line having a low brightness sum is likely a short line through muscle tissue, terminating at the fat layer surrounding the rib eye muscle or a blob of intramuscular fat. The line representing the most likely cutting path is therefore the line having the lowest brightness sum.

If the lowest sum line still has a relatively high brightness sum (above a selected threshold), a cut will not be made as the proposed cut line is long, and therefore probably projects substantially into the interior of the rib eye muscle rather than towards the edge. If the proposed cut line is below the threshold sum brightness, a cut will be considered further.

As shown in FIG. 27, a small ellipse 266, substantially smaller than ellipse 250, is plotted inside ellipse 250. The small ellipse 266 is sufficiently small that it will always fall inside the rib eye muscle outline. If the start point or end point of a proposed cut would fall within the small ellipse, the cut is rejected. If neither the start point or end point of the proposed cut would fall within the small ellipse, a cut is made.

Using this process, accurate cuts can be made to exclude extraneous muscle tissue from the traced rib eye muscle outline. As shown in FIG. 19, the boundary between an extraneous muscle segment 206 and the rib eye muscle 200 is often dotted with a chain of small fat globules forming an interstitial seam of fat 268. The cut analysis technique described above will select a series of short cuts from one fat globule to the next, which, in most cases, will fairly accurately describe the rib eye muscle edge.

c. Confirming Edge Tracing

In certain cases, particularly where there is no interstitial seam of fat between the rib eye muscle and a piece of extraneous muscle tissue, the process described in the previous step will fail to cut off a piece of extraneous muscle tissue. A technique described herein as progressive angle analysis is therefore used as a safeguard against missed cuts.

As shown in FIG. 29, a line 270 is projected from the centre 272 of the ellipse 250 (shown in FIG. 27) to each point along the traced rib eye muscle edge, progressing consecutively in a counter-clockwise direction, starting from an arbitrary point of origin 274. As the traced rib eye muscle edge is a generally regular shape, with few sharp turns, line 270 will appear to sweep in a counter-clockwise direction through points 274–282. Angle 284 will therefore continue to increase as the sweep of line 270 progresses. Between points 282 and 286, the sweep of line 270 will reverse and move in a clockwise direction. Angle 284 will therefore become smaller. Between points 286 and 288, angle 284 will once again increase. Point 288 is co-linear with points 272 and 282. The change in angle 284 indicates the location of the sharp turn at 282.

As shown in FIG. 30, as in step IV(C) (8) (a), the sharp turn at point 282 is bisected, and a series of radiating lines 290 are projected. Unlike step IV(C) (8) (a), the lines 290 do not terminate when fat is reached, but rather when the rib eye muscle outline 205 is reached. The shortest line 290, that being the line 290 to point 292 is selected for possible cutting.

Cutting along line 290 from point 282 to point 292 would cut off muscle segment 294. The longest axis 296 of muscle segment 294 is determined. If line 290 is less than approximately half the length of line 296, the next criteria for cutting is examined. If line 290 is greater than approximately half the length of 296, a cut is not made.

The edge of muscle segment 294 (along the traced rib eye muscle outline between points 282 and 292) is approximated as a series of short straight lines, each about 20 pixels in length, to define a many-sided polygon. The polygon is broken into triangles, and a triangle area formula is used to determine the area of each triangle in the polygon. The sum of the areas of the triangles making up the polygon equals the area of the polygon and is used as an estimate of the area of muscle segment 294. The proportion of the area of muscle segment 294 that falls inside projected ellipse 250 is determined. The proposed cut will be rejected if any of the following criteria are met:

the area of muscle segment 294 that falls outside projected ellipse 250 is greater than 15 cm$^2$ (on 1:1 scale with actual rib eye);

the area of the rib eye outline that would remain after excision of muscle segment 294 would be less than 50 cm$^2$ (on 1:1 scale with actual rib eye); or less than one half of the total area of muscle segment 294 falls outside projected ellipse 250.

If none of these criteria are met, a cut is made.

9. Determining the Area of the Traced Rib Eye Muscle

After tracing of the rib eye muscle outline has been completed, the number of pixels on each row within the traced rib eye muscle outline on the IMap is tabulated. This data is readily correlated with the image size information derived during camera calibration. Each pixel within the rib eye muscle outline is determined to be either a fat pixel or a muscle tissue pixel on the basis of brightness thresholding.

The full colour information of pixels in the original acquired image corresponding to muscle tissue pixels identified in the IMap are recorded and used to calculate an accurate average colour of the rib eye muscle tissue. The average rib eye muscle tissue colour is corrected with the colour information obtained during camera calibration. Average rib eye muscle tissue colour information may be used for meat grading purposes.

As the number of fat pixels within the rib eye muscle outline is known, the proportion of intramuscular fat, or marbling, can be readily determined by dividing the number of fat pixels within the rib eye muscle outline by the total number of pixels within the rib eye muscle outline.

All intramuscular fat pixels are subjected to blob analysis, as described previously. Blobs of fat larger than a selected threshold size are eliminated from the calculation of the percentage marbling.

10. Determining the Thickness of the Subcutaneous Fat Layer

Figure 31:
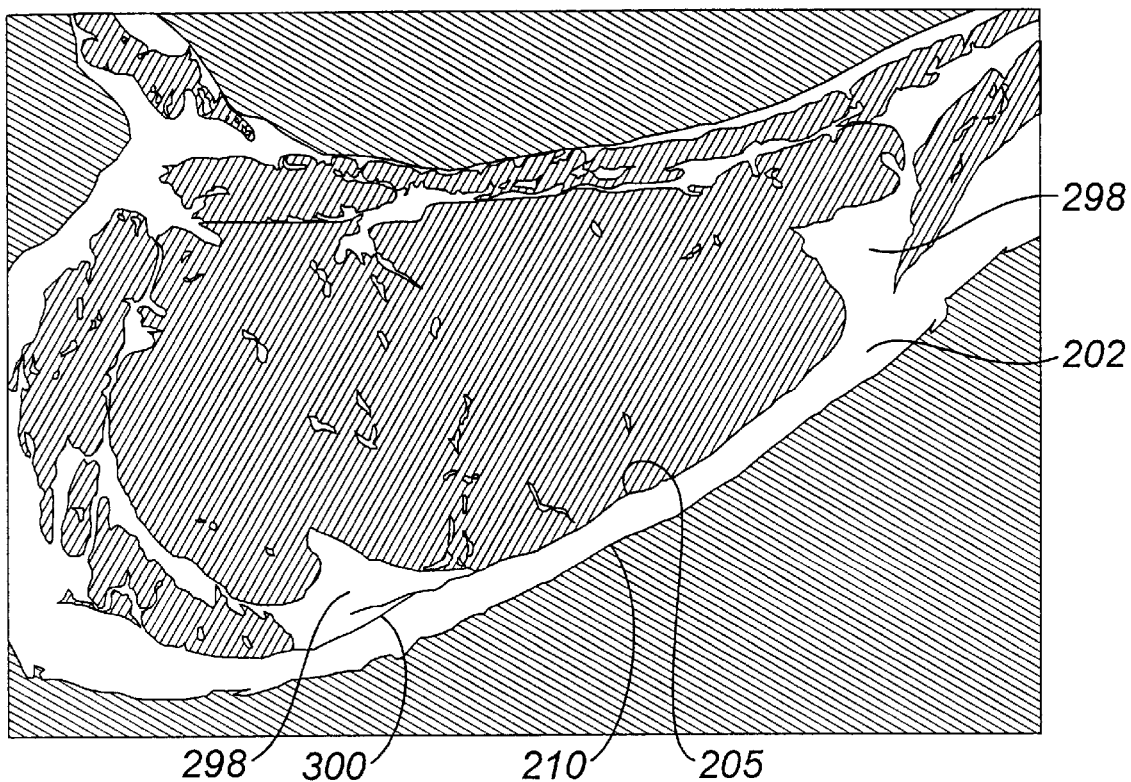
FIG. 31 shows further details of a rib eye image.

As shown in FIG. 31, it may be difficult to distinguish the layer of subcutaneous fat 202 used for grading purposes from other fat 298. The subcutaneous fat layer 202 is bounded by the rib eye muscle outline 205, and the fat edge 210 traced in step IV(C) (1). Generally, a fine dark line 300 may be detected separating the subcutaneous fat layer 202 from the other fat 298.

Figure 32:
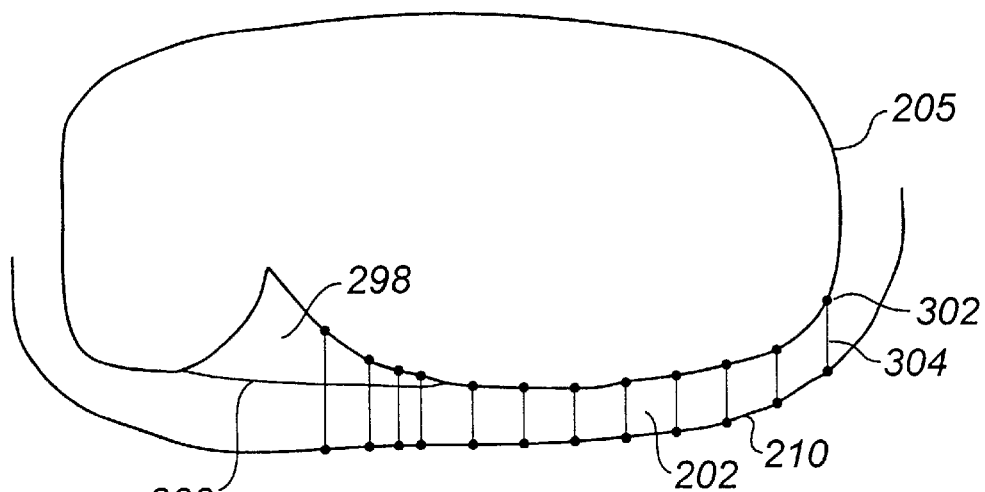
FIGS. 32–35 illustrate steps in making grading measurements from the traced rib eye outline.

As shown in FIG. 32, starting from the right-most pixel column 302 on the rib eye muscle outline 205, the length of the line 304 between the fat edge 210 and the rib eye muscle outline 205 is determined. The length of line 304 defines the thickness of the subcutaneous fat layer 202 in the right-most pixel column 302 on the rib eye muscle outline 205.

Using the same method, the thickness of the subcutaneous fat layer 202 is measured at approximately 3 mm (measurement on rib eye muscle) intervals, working leftward. Typically, the other fat 298 is present primarily on the left side of the rib eye muscle image (left side of carcass rib eye muscle) and is not found on the right side of the rib eye muscle. The thickness of the subcutaneous fat layer 202 is therefore most easily determined on the right side of the rib eye image.

Using a mask LLHHHHH, an attempt is made to locate fine dark line 300 by searching upward along columns at five column intervals, working leftward. If a fine dark line 300 is found, it is used to define the inside edge of the subcutaneous fat layer 202 by connecting the points found along the fine dark line 300. This defined inside edge is rejected if it would result in the thickness of the subcutaneous fat layer at the left side of the image being substantially different than the average thickness of the subcutaneous fat layer at the right side of the image.

If no fine dark line 300 can be detected, or is too faint to be reliably detected, the position of the inner edge of the subcutaneous fat layer 202 where it meets other fat 298 (which would be in the same position as fine dark line 300) is estimated to be the same as the average thickness of the subcutaneous fat layer at the right side of the image, where there is little likelihood of encountering other fat 298. A line is therefore plotted a distance upward of the fat edge 210 that represents the average thickness of the subcutaneous fat layer at the right side of the image.

The inner fat edge is then smoothed out using the process described in step IV(C) (1).

11. Determining the Length of the Rib Eye Muscle

Figure 33A:
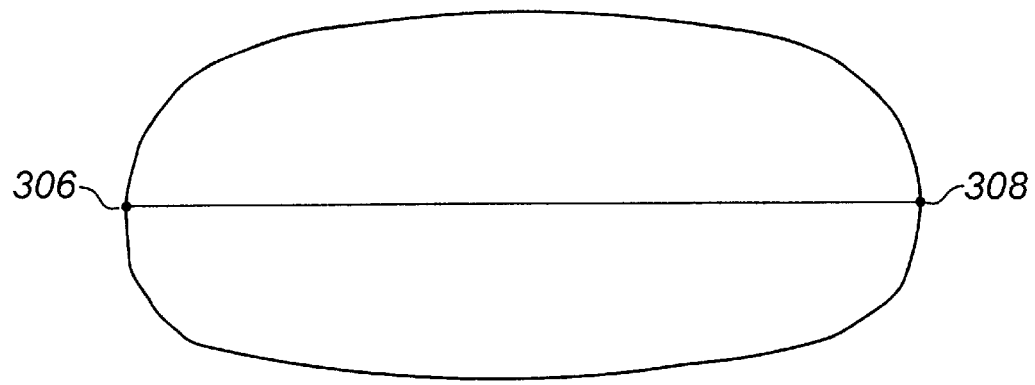
Figure 33B:
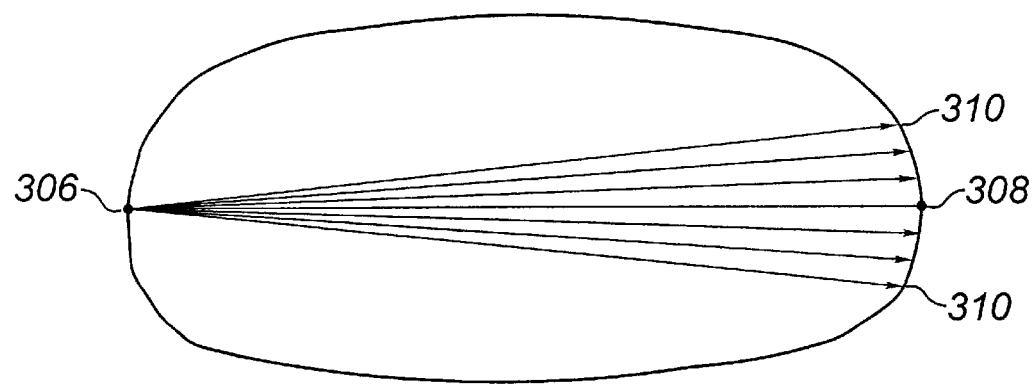
Figure 33C:
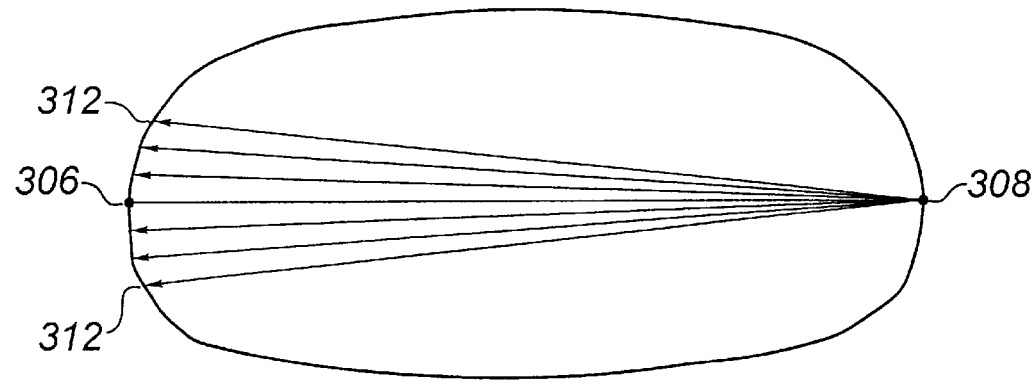

As shown in FIGS. 33A to 33C, the left-most 306 and right-most 308 points on the rib eye muscle outline are selected. A series of lines are projected from point 306 to a range of points 310 along the rib eye muscle outline near point 308. The length of each line from point 306 to point 310 is compared with the length of the line from point 306 to point 308 to determine which line is longest.

Similarly, a series of lines are projected from point 308 to a range of points 312 along the rib eye muscle outline near point 306. The length of each line from point 308 to point 312 is compared with the length of the line having endpoints 308 and 306 to determine which line is longest.

The longest line detected above defines the rib eye muscle length.

12. Determining the Width of the Rib Eye Muscle

Figure 34:
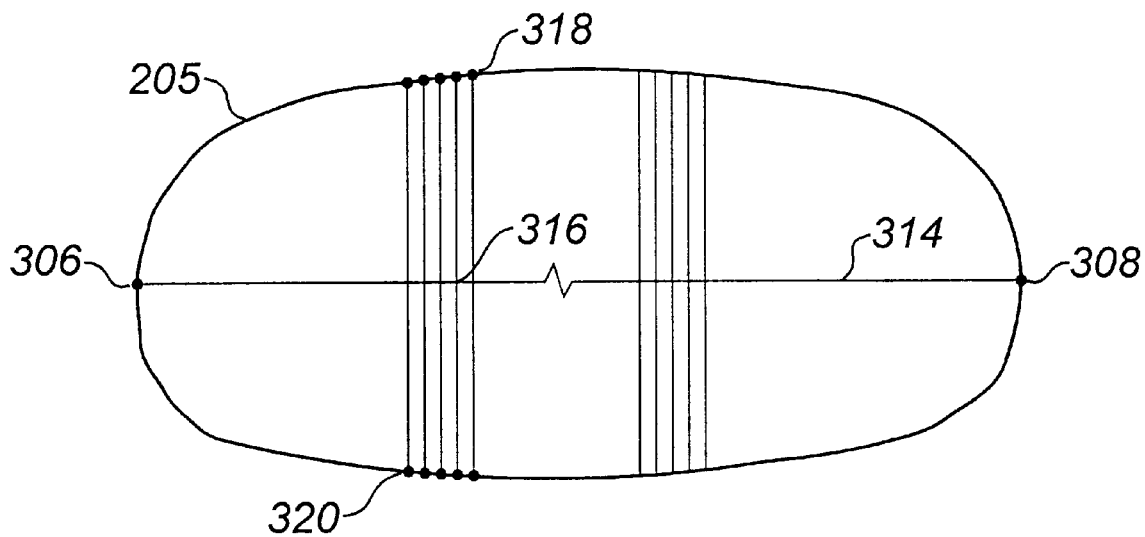

As shown in FIG. 34, line 314 defining the length of the rib eye muscle is divided into numerous (approximately 200) equal divisions 316. The distance from each point 318 on the traced rib eye muscle outline 205 above line 314 in the column of pixels at each division 316 is added to the distance from each point 320 on the traced rib eye muscle outline 205 below line 314 in the column of pixels at each division 316. The column having the greatest total length from point 318 to line 314 plus line 314 to point 320 defines the rib eye muscle width.

As a safeguard, the width measurement is rejected if it falls on a column outside of the centre 50% of the length of the rib eye muscle.

13. Measuring the Thickness of the Subcutaneous Fat Layer for Grading Purposes Once the length of the rib eye muscle has been determined, this information, in conjunction with the data collected in step IV(C) (10) about the thickness of the subcutaneous fat layer, can be used for grading analysis.

Figure 35:
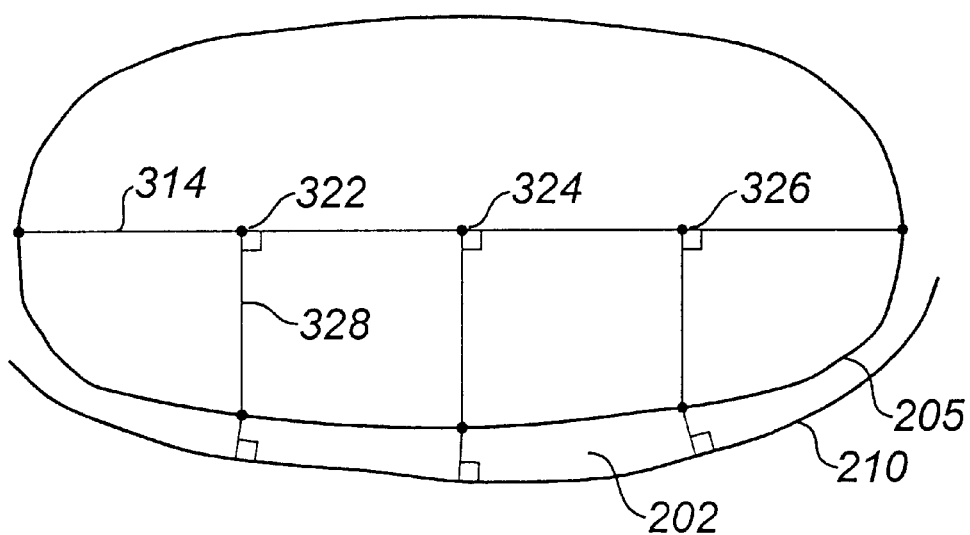

Grading analysis will vary according to beef grading practices in various jurisdictions. In Canada, for instance, as shown in FIG. 35, the line describing the length of the rib eye muscle 314 is divided into four equal sections, thereby defining points 322, 324 and 326. At each of points 322, 324 and 326, a line 328 is plotted downward, perpendicular to line 314, to intersect the inner edge of the subcutaneous fat layer 202 (that being the rib eye outline 205). The thickness of the subcutaneous fat layer 202 is determined along each line 328 through points 322, 324 and 326, by calculating the distance between the inner edge of the subcutaneous fat layer 202 (that being the rib eye outline 205) and the outer edge 210 of the subcutaneous fat layer 202, perpendicular to the outer edge 210. The minimum thickness of the subcutaneous fat layer in the right quadrant, representing the standard "grade fat" measurement, is also determined. This information is used in determining the yield grade of the carcass.

V. Analysis of Data Collected by the Hot Carcass Imaging System and the Rib Eye Muscle Imaging System The measurements obtained from the carcass imaging system and the rib eye imaging system are useful as independent variables in predictive equations to predict various carcass parameters. Predictive equations may include independent variables consisting of measurements taken only from the whole carcass (one side only), only from the rib eye, or may include measurements taken from both the whole carcass and the rib eye image.

Carcass parameters of particular interest include those which are indicative of the commercial value of the carcass. As described in the Examples herein, predictive equations have been developed to predict the saleable yield of beef carcasses. Other carcass parameters of interest include, without limitation, lean body mass and carcass yield. Lean body mass may be defined as the total mass of skeletal muscle in an animal or as the proportion of the entire live weight of the animal represented by skeletal muscle. Carcass yield may be defined as the combined mass of skeletal muscle, bone and associated fat as a proportion of live animal weight. This value is commonly expressed as a percentage (e.g. 60% carcass yield) or as a weight relationship (e.g. 600 g/kg live weight).

In developing a predictive equation, carcass image and rib eye image analysis as described hereinabove is performed on a sample population of carcasses and the value of the carcass parameter of interest is measured for each carcass. The sample population contains a sufficient number of carcasses that a statistically significant relationship or correlation between one or more of the selected independent variables and the carcass parameter (dependent variable) of interest can be determined. The sample population may contain as few as three carcasses, and more preferably greater than ten carcasses, and still more preferably, greater than 100 carcasses.

The relationship between the independent variables and the dependent variables can be determined by any of a number of known statistical methods such as multiple linear regression, Artificial Neural Net learning, cluster analysis and discriminant analysis. In a preferred embodiment, the multiple regression procedure of SAS (SAS Institute Inc., Cary, N.C.) is used. Where there are multiple independent variables, a solution utilizing matrix algebra may be used. For instance, where nine independent variables are being analysed, and the dependent variable is saleable yield, the multiple regression model may be:

$$y_j = a + b_1 x_{1j} + b_2 x_{2j} + b_3 x_{3j} + b_4 x_{4j} + b_5 x_{5j} +$$

$$b_6 x_{6j} + b_7 x_{7j} + b_8 x_{8j} + b_9 x_{9j} + e_j = a + \sum_{i=1}^{9} b_i x_{ij} + e_j$$

where:

$y_j$=the sealable yield of the j-th animal j=1, 2 . . . 9, a=the overall mean, $b_i$=the i-th regression coefficient, i=1, 2 . . . 9, $x_j$=the j-th predictor variable, j=1,2, . . . 9, $e_j$=random error associated with the j-th observation.

The following matrix and vectors are defined:

$$x = \begin{bmatrix} 1 & x_{11} & x_{21} & \ldots & x_{91} \\ 1 & x_{12} & x_{22} & \ldots & x_{92} \\ \vdots & \vdots & \vdots & \ddots & \vdots \\ 1 & x_{1n} & x_{2n} & \ldots & x_{9n} \end{bmatrix}, y = \begin{bmatrix} y_1 \\ y_2 \\ \vdots \\ y_n \end{bmatrix}, e = \begin{bmatrix} e_1 \\ e_2 \\ \vdots \\ e_n \end{bmatrix}, \text{and } b = \begin{bmatrix} b_1 \\ b_2 \\ \vdots \\ b_n \end{bmatrix}$$

The complete set of equations is y=Xb+e with E(y), E(e)=0 and var(e)=$\sigma^2$ I, where E denotes the expectation operator and $\sigma^2$ is a constant.

The regression coefficient b is estimated as, $$b=(X'X)^{-1}X'y$$

The prediction is $$y = a + \sum_{i=1}^{9} b_i x_{ij}$$

Information taken from the rib eye analysis alone may also be used to derive a predictive equation for a carcass parameter such as saleable yield as described above. Alternatively, the rib eye analysis information may be used to determine a quality grade for the carcass. As discussed previously, North American quality grading of carcasses into grades such as A, AA, and AAA generally depends on the percentage of intramuscular fat (marbling) of the carcass, as estimated from the rib eye. As the accurate tracing and muscle tissue/fat discrimination techniques of the present invention permit accurate assessment of the percentage of intramuscular fat in the rib eye, the rib eye analysis techniques of the invention are useful for determining quality grades of carcasses.

The invention is further illustrated by the following non-limiting examples.

EXAMPLE 1

An apparatus and process of the invention was tested to evaluate the accuracy of the rib eye imaging system in determining rib eye parameters. For convenience, the embodiment of the invention tested in the following examples is referred to herein by the inventors' designation "Lacombe CVS".

Rib eye images were obtained and analysed with the Lacombe CVS from 40 beef cattle carcasses. The rib eyes were then manually traced by human graders and measured using a grading grid. As shown in Table 3, the Lacombe CVS tracing of the rib eye area correlated closely with the manual tracing. Squaring the correlation provides the $R^2$ value.

TABLE 3

Correlation of CVS traced rib eye area and graders' estimates

|  | Graders' grid area | Graders' traced area |
|---|---|---|
| Computer traced area | 0.89 | 0.87 |

EXAMPLE 2

A total of 65 carcasses, representing 19, 19 and 22 carcasses of A, AA and AAA grade, respectively were sampled and railed to the back of the grading stand for further measurement (Table 5). A certified grader assessed the quality grade and marbling in AMSA (American Meat Science Association) units directly from the carcass and again from the captured image displayed on the computer screen.

Images of United States Department of Agriculture marbling standard photographs were analysed with the Lacombe CVS in order to calibrate the CVS to make quality grade determinations. The estimated percentage of intra-muscular fat as determined by the CVS for Canadian and U.S. quality grades is set forth in Table 4.

TABLE 4

Lacombe CVS etimates of USDA marbling standard

| Canada quality grade | US quality grade | Lacombe CVS estimated % intra-muscular fat |
| --- | --- | --- |
| AA | Slight | 0.9% |
| AAA | Small | 2.0% |
| Canada Prime | Slightly Abundant | 9.7% |

The rule for assigning quality grade is shown in Table 5.

TABLE 5

Lacombe CVS rules for assigning Canadian quality grade

| Grade | Rules |
| --- | --- |
| B1 | 0% CVS marbling |
| A | 0% < CVS marbling % < 0.9% |
| AA | 0.9% ≤ CVS marbling % < 2.0% |
| AAA | 2.0% ≤ CVS marbling % < 9.7% |
| Canada Prime | 9.7% ≤ CVS marbling % |

Table 6 shows the CVS % marbling determinations, the AMSA scores determined by the certified grader directly from the carcass and as determined from the CVS computer screen.

TABLE 6

Percent marbling by quality grade

|  | A | AA | AAA |
| --- | --- | --- | --- |
| Number of carcasses | 19 | 19 | 22 |
| Computer % marbling | 2.73 ± 1.20 | 4.90 ± 1.12 | 6.33 ± 1.70 |
| AMSA | 289.47 ± 36.13 | 487.89 ± 29.92 | 542.27 ± 63.39 |
| Screen AMSA | 427.50 ± 53.23 | 521.25 ± 33.64 | 563.33 ± 71.39 |

The correlation of CVS estimated marbling % with grader's AMSA in real time was 0.81 (Table 7). The correlation improved to 0.92 when the grader graded the carcasses again from the computer screen.

TABLE 7

Correlations between CVS % marbling estimate and grader's AMSA score

| AMSA | .81 |
| --- | --- |
| Screen AMSA | .92 |
| Based on n = 65 | |

EXAMPLE 3

The Lacombe CVS was tested to determine whether consistent grading determinations could be made on the same carcass rib eye under different lighting conditions.

44 beef steaks having varying levels of marbling were purchased from super markets. Each steak was analysed 5 times at the Lacombe Meat Research Centre in Lacombe, Alberta, Canada in the cutting room, in a meat cooler, and in a display case. These areas represent lighting conditions of bright fluorescent light, dimmed fluorescent light and incandescent light, respectively.

As shown in Table 8, the repeatability estimates for rib eye area and % marbling ranged from 0.86 to 0.96, indicating that the rib eye imaging system can provide consistent results under different lighting conditions. The repeatability estimates for grade fat were lower because the steaks were kept at room temperature and were therefore very soft and changed shape when they were moved from one location to another.

TABLE 8

Repeatability of Lacombe CVS measurements in various lighting conditions

| | Location | | |
| --- | --- | --- | --- |
| CVS measurements | Cutting room | Meat Cooler | Display case |
| Grade fat | 0.66 | 0.84 | 0.44 |
| Rib eye area | 0.96 | 0.96 | 0.86 |
| Marbling % | 0.96 | 0.96 | 0.96 |

EXAMPLE 4

A second study was conducted to assess the repeatability of measurements taken by the Lacombe CVS. On the first day of the study, a human grader made standard measurements of grade fat, rib eye area and marbling on the rib eyes of 14 carcasses using a measuring grid. The carcasses were then measured twice within a minute by the CVS. The carcasses were manually pushed one at a time to be measured by the rib eye camera. On the second day of the study, essentially the same procedures were carried out on 21 additional carcasses.

Table 9 shows the correlation between the two successive measurements taken by the Lacombe CVS on each carcass. Overall, the average correlation can be seen to be very high, close to 97%.

TABLE 9

Correlation of two repeated CVS measurements

| Correlation between | Study 1 (n = 14) | Study 2 (n = 21) |
|---|---|---|
| CVS first and second grade fat measurements | 0.98 | 0.97 |
| CVS first and second rib eye area measurements | 0.98 | 0.98 |
| CVS first and second marbling measurements | 0.97 | 0.94 |

EXAMPLE 5

A further repeatability study was conducted in which grade fat, rib eye area and % marbling were measured for rib eyes of 166 beef carcasses with the Lacombe CVS. Measurements were repeated between 1 and 11 times, with a mean of 4 repeated measurements. The carcasses were also graded by human graders. A total of 166 head of beef cattle, representing carcasses from 2 sexes by 3 weight groups by 3 fatness levels, were sampled. Data collection was completed in a 3-day cycle. In the first day of the data cycle, images were obtained of intact carcasses, prior to chilling. Poor quality images were noted so those carcasses were not selected for cutout the next day. In the second day, carcasses were selected according to a pre-planned sampling scheme. Rib eye images from chilled carcasses were obtained and human graders' grades were recorded. In the third day, the selected carcasses were cut out (dissected) by a crew of 7 cutters who dissected 20 left half carcasses to ¼" trim saleable yield in 3 hours. Technicians supervised the cutout and recorded weights of various cuts.

The carcass cutout data were assembled and edited. Saleable meat yield was defined as the sum of the cut weights plus the weights of the trim (50, 75 and 85% lean) expressed as a percentage of the side weight. The data from image analysis were merged.

As shown in Table 10, the repeatability for grade fat, rib eye area and % marbling were all greater than 0.95.

TABLE 10

Repeatability of CVS measurements

| CVS measurements | Repeatability |
|---|---|
| Grade fat | 0.99 |
| Rib eye area | 0.95 |
| Marbling % | 0.95 |

EXAMPLE 6

Correlations between Lacombe CVS and human grader measurements for grade fat thickness and rib eye area were determined for the data collected in Examples 2 and 3. As shown in Table 11, correlations between the Lacombe CVS and grader measurements ranged from 0.89 to 0.99 in 3 separate studies.

TABLE 11

Correlation between CVS and grader measurements

| Between CVS and grader measurement for | Study 1 (n = 14) | Study 2 (n = 21) | Study 3 (n = 166) |
|---|---|---|---|
| Grade fat | 0.89 | 0.96 | 0.95 |
| Rib eye area | 0.91 | 0.99 | 0.95 |

EXAMPLE 7

The degree of correlation between human grader marbling (quality grade) determinations and those of the Lacombe CVS was determined. The CVS marbling percent estimation was calibrated with the regional grading supervisor, Food Protection & Inspection Branch, Agriculture and Agri-Food Canada. The threshold for deciding whether a pixel is muscle or fat was adjusted by trial and error in an effort to mimic the marbling levels seen by the grader. After the adjustment was complete, a test was conducted to determine the correspondence between the marbling grade assigned by the CVS and by the grading supervisor. Out of a total of 62 carcasses tested, mostly AA and AAA grades, only 4 were in disagreement. This suggests that the Lacombe CVS can be calibrated to match an experienced grader to a reasonable level of accuracy.

EXAMPLE 8

Saleable yield predictive equations were determined using the data acquired in Example 5. Hip, sirloin, loin, rib, chuck, flank, plate and brisket primal cuts were determined on carcass images as described in step III(B)(4)(c) in the Detailed Description of the Preferred Embodiment. As described in step III(B)(4)(d) of the Detailed Description of the Preferred Embodiment and shown in FIG. 17, the carcass images were divided into six linear regions described as the hind leg, lower hip, upper hip, lower back, mid back and shoulder linear regions. Each linear region was divided into 10 equal divisions, demarcated by lines plotted transversely to the long axis of the carcass image. In each linear region, the transverse lines were assigned reference numbers 1–9, starting at the posterior end of the carcass image. The distance from the points where each transverse line intersected the ventral and dorsal regions of the carcass image outline to the mid-line (line b3–b9 in FIG. 17) were determined.

Angular measurements and curvature measurements as described in steps III(B)(4)(e) and (f) were also determined. In total, in excess of 400 carcass and rib eye measurements were made and tested for correlation with carcass saleable yield.

Stepwise regression was applied to the data to arrive at the best models to predict saleable yield from intact carcass measurements, rib eye measurements and the combination of these two sets of measurements. The $R^2$ (multiple correlation squared), which indicates how well the data fit the model, and residual standard deviation (square root of the residual mean square), which indicates the error of predicting the cutout value from CVS measurements, are summarized in Table 12. The accuracy of the Lacombe CVS (RSD=1.03%) to predict saleable yield was higher than the Australian system evaluated by Jones et al. (1993, RSD= 1.27%) and Richmond et al. (1995, RSD=1.65%). The most accurate results were obtained when measurements both from the intact carcass image and from the rib eye image were included as independent variables in the predictive equation. The use of 20 measurements from the carcass image alone proved to be the next most accurate approach, followed by 5 CVS measurements only from the rib eye. Notably, all saleable yield equations determined using CVS measurements proved to be of greater accuracy than equations based upon measurements made by a human grader.

TABLE 12

Accuracy of using computer vision measurements to predict % saleable yield

| Measurements included in the model | $R^2$* | RSD (%)** |
|---|---|---|
| Based on grader's measurements at grading site | 0.57 | 1.55 |
| Based on 20 carcass measurements alone | 0.67 | 1.46 |
| Based on 5 rib eye measurements at grading site | 0.61 | 1.49 |
| Based on a combination of 20 carcass and 5 rib eye measurements | 0.84 | 1.03 |

*multiple correlation squared
**RSD-residual standard deviation

The saleable yield prediction equation based upon rib eye measurements only was determined to be:

% saleable yield=76.238706+0.010197$T_{AREA}$−0.349852$TP_{FAT}$− 0.427767 $A_{FAT}$+0.25422$M_{FAT}$−0.193396$G_{FAT}$ where:

$T_{AREA}$=total area of the rib eye;
$TP_{FAT}$=total percentage of intramuscular fat in the rib eye;
$A_{FAT}$=average of rib eye subcutaneous fat thickness measurements at top, mid, and bottom points as shown in FIG. 35, reference numbers 322, 324, and 326;
$M_{FAT}$=subcutaneous fat thickness at mid point as shown in FIG. 35 at reference number 324; and
$G_{FAT}$=subcutaneous fat thickness at the standard grade fat measurement point, being the minimum subcutaneous fat thickness in the right-most quadrant as shown in FIG. 35.

The saleable yield predictive equation based upon carcass measurements only was determined to be:

% Saleable yield = 106.085803− 176.062150 $P_{RIB}$ +

262.044441 $P_{LOIN}$ − 340.168645 $P_{PLATE}$ − 270.060083 $A4$ +

295.14395 $A6$ + 32.222714 $HIND3$ + 24.016820 $HIND22$ +

7.035919 $L_{HIP34}$ − 51.034738 $L_{HIP35}$ + 14.944928 $M_{BACK3}$ −

27.824773 $M − BACK12$ − 89.700540 $SHLD2$ +

73.786202 $SHLD6$ − 15.522698 $SHLD23$ + 35.014305 $CW_{LB}$ where:

$P_{RIB}$=ratio of the area of the rib primal cut to total carcass image area;
$P_{LOIN}$=ratio of the area of the loin primal cut to total carcass image area;
$P_{PLATE}$=ratio of the area of the plate primal cut to the total carcass image area;
$A4$=area of loin primal cut;
$A6$=area of plate primal cut;
HIND3=ventral distance to mid-line for interval 1 in the hind leg linear region;
HIND22=dorsal distance to mid-line for interval 6 in the hind leg linear region;
$L_{HIP8}$ =carcass width for interval 2 in the lower hip linear region;
$L_{HIP34}$ =dorsal distance for interval 9 in the lower hip linear region;
$L_{HIP35}$ =ventral distance for interval 9 in the lower hip linear region;
$M_{BACK3}$ =ventral distance for interval 1 in the mid-back linear region;
$M_{BACK12}$ =carcass width for interval 3 in the mid-back linear region;
SHLD2=dorsal distance for interval 1 in the shoulder linear region;
SHLD23=dorsal distance for interval 6 in the shoulder linear region; and
$CW_{LB}$=average carcass width in the lower back linear region.

The saleable yield predictive equation using measurements from both the whole carcass and the rib eye as independent variables was determined to be:

% Saleable yield = 79.448902+ 0.018258 $T_{AREA}$ − 0.191083 $TP_{FAT}$ −

0.362784 $A_{FAT}$ + 0.267664 $M_{FAT}$ − 0.185617 $G_{FAT}$ − 20.087953 $P_{RIB}$ +

214.213295 $P_{LOIN}$ − 243.441006 $P_{PLATE}$ − 224.112984 $A4$ +

171.424092 $A6$ + 13.781479 $HIND3$ + 14.152217 $HIND22$ +

2.862327 $L_{HIP8}$ − 20.933690 $L_{HIP34}$ − 25.216945 $L_{HIP35}$ +

2.567813 $M_{BACK3}$ − 1.173930 $M_{BACK12}$ − 59.559750 $SHLD2$ +

45.429554 $SHLD6$ − 11.739671 $SHLD23$ + 41.817415 $CW_{LB}$ wherein the independent variables are as set forth above.

It will be noted in the above predictive equations for saleable yield that none of the oblique angle measurements or curvature measurements proved to be closely associated with saleable yield of beef carcasses in this instance. Further, it is somewhat surprising that the area of the plate primal cut and the ratio of the area of the plate primal cut to the total carcass outline area proved to be important variables, in that the plate primal cut is of lesser economic importance than other primal cuts from the beef carcass. It will further be noted that the saleable yield predictive equations include at least two distances from each of the ventral and dorsal regions of the carcass image outline to the mid-line, at least two carcass widths, and primal cut areas and the ratios of primal cut areas to the total carcass image area.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practised within the scope of the appended claims.

We claim:

1. A process for determining a quality grade of an animal carcass, comprising the steps of:
   (a) obtaining an image which includes the rib eye of the carcass, the image being composed of an array of pixels providing colour data representative of colour information at the corresponding part of the image;
   (b) discriminating pixels representing muscle tissue from pixels representing fat tissue on the basis of a pixel colour characteristic threshold;
   (c) identifying a cluster of muscle tissue pixels within the image that represents the rib eye and tracing the outline of the rib eye muscle to exclude external image sections representing muscle tissue which abuts but is not part of the rib eye;
   (d) determining the proportion of pixels within the rib eye outline representing fat relative to the total number of pixels within the rib eye outline to obtain a value of the percentage of intramuscular fat in the rib eye;
   (e) repeating steps (b) through (d) for a plurality of reference images of rib eyes of carcasses of pre-determined quality grade to establish a relationship between the percentage of intramuscular fat in the rib eye and the quality grade of the carcass; and
   (f) solving the relationship determined in step (e) for the value of the percentage of intramuscular fat in the rib eye determined in step (d) to determine the quality grade of the carcass.

2. The process of claim 1 comprising the further step of discriminating pixels representing muscle tissue from pixels which do not represent muscle tissue or fat tissue on the basis of a pixel colour saturation level threshold.

3. The process of claim 1 wherein in step (e), the reference images of rib eyes are obtained from standard photographs showing the appearance of rib eyes of carcasses of known quality grades.

4. A process for determining parameters of a rib eye of a carcass, comprising the steps of:
   (a) obtaining an image which includes the rib eye of the carcass, the image being composed of an array of pixels providing colour data representative of colour information at the corresponding part of the image;
   (b) discriminating pixels representing muscle tissue from pixels representing fat tissue on the basis of a pixel colour characteristic threshold;
   (c) identifying a target cluster of contiguous muscle tissue pixels within the image, the target cluster including the rib eye, and tracing the outline of the cluster of muscle tissue pixels including the rib eye;
   (d) identifying and excising external image sections representing muscle tissue which abuts but is not part of the rib eye, the step of identifying external image sections including:
      (i) identifying outward turns in the rib eye outline traced in step (c); and
      (ii) rejecting an outward turn as a potential site to commence a cut to excise an external image section if a first line bisecting the turn would not be substantially parallel to a second line tangent to a first generally elliptical figure surrounding the rib eye outline at a point on the ellipse collinear with the centre of the elliptical figure and the vertex of the turn.

5. The process of claim 4, wherein identifying and excising step (d) further comprises:
   (iii) plotting a plurality of search lines originating from the vertices of outward turns which were not rejected in step (ii), the search lines radiating inwardly through a range of at least about 20° on either side of a line bisecting the turn; recording the number of pixels representing muscle tissue along each search line until a string of at least about 4 consecutive pixels representing fat is detected; and selecting the search line having the fewest pixels representing muscle tissue as a potential path of a cut to excise an external image section.

6. The process of claim 5, wherein step (d)(iii) further comprises rejecting the selected search line as a potential path of a cut to excise an external image section if the path of the cut would intersect a second generally elliptical figure contained wholly within the rib eye muscle outline.

7. The process of any of claims 4, 5, or 6, comprising the further step of:
   (e) identifying and excising remaining external image sections that were not identified and excised in step (d) by:
      (i) identifying any remaining outward turns in the rib eye image outline;
      (ii) plotting a plurality of search lines originating from the vertices of each remaining outward turn on the rib eye image outline, the search lines radiating inwardly through a range of at least about 20° on either side of a line bisecting the turn;
      (iii) recording the number of pixels along each search line to determine the length of the search line until the search line again intersects the rib eye image outline;
      (iv) selecting the search line having the shortest length as a potential path of a cut to excise an external image section.

8. The process of claim 7 wherein identifying remaining outward turn step (e)(i) comprises plotting the path of a target travelling along the rib eye image outline and measuring the radial movement of a line having end points on the target and the centre of the rib eye image outline, an outward turn being detected at the point on the outline occupied by the target when the movement of the line between the target and the centre of the rib eye line reverses direction of rotation.

9. The process of claim 8 wherein identifying and excising step (e) further comprises:
   (v) rejecting the potential path of a cut to excise an external image section if the length of the path is greater than a pre-determined proportion of the length of the longest axis of the external image section to be excised.

10. The process of claim 9 wherein identifying and excising step (e) further comprises:
    (vi) rejecting the potential path of a cut to excise an external image section if at least one of the following criteria is met:
       (1) the external image section that would be excised by the cut would have greater than a pre-determined area;
       (2) the cut would result in a rib eye image outline having less than a pre-determined area; or
       (3) less than a pre-determined percentage of the area of the external image section that would be excised by the cut would fall outside the first generally elliptical figure.

11. The process of any one of claims 4 to 10 comprising the further step:

(f) after excising any external image sections, determining the proportion of pixels within the rib eye outline representing fat relative to the total number of pixels within the rib eye outline to obtain a value of the percentage of intramuscular fat in the rib eye.

12. A process for determining grading parameters of a carcass, comprising the steps of:

(a) obtaining an image of a view of the carcass, the image being composed of an array of pixels providing data representative of information at the corresponding part of the image;

(b) tracing the outline of the image to produce a carcass image outline;

(c) locating a plurality of first reference points on the carcass image outline, the first reference points representing anatomical features of the carcass, the anatomical features being identified as protrusions or indentations in the carcass image outline;

(d) locating at least one second reference point on or within the carcass image outline, the second reference points being located at pre-determined positions relative to the first reference points;

(e) dividing the carcass image into a plurality of sections, the boundaries of each section being determined as a function of the position of the first and second reference points, and determining the area of each section;

(f) providing a grading parameter predictive equation wherein the grading parameter is included as a dependent variable, and at least one area of a section determined in step (e) is included as an independent variable; and, (g) solving the grading parameter predictive equation to provide a value for the grading parameter of the carcass.

13. The process of claim 12 further comprising the step of:

(h) determining the shortest distance from at least one reference point on a dorsal or ventral region of the carcass image outline to a carcass image mid-line plotted substantially parallel to the long-axis of the carcass image, the mid-line dividing the carcass image into ventral and dorsal portions;

and wherein at least one of the distances from the reference points on the dorsal or ventral regions of the carcass image outline to the mid-line determined in step (h) is included as an independent variable in the grading parameter predictive equation provided in step (f).

14. The process of claim 13 further comprising the step of:

(i) determining the width of the carcass image outline at at least one reference point, perpendicular to the mid-line established in step (h);

and wherein at least one of the widths of the carcass image outline determined in step (i) is included as an independent variable in the grading parameter predictive equation provided in step (f).

15. The process of claim 14 wherein step (e) further comprises determining the ratio of the area of at least one of the carcass image sections to the total area encompassed by the carcass image outline, and wherein at least one of the ratios is included as an independent variable in the grading parameter predictive equation provided in step (f).

16. The process of claim 15 wherein in step (e), the sections include sections having the boundaries of standard primal cuts used in a carcass grading system, the primal cuts selected from the group consisting of hip, sirloin, loin, rib, chuck, flank, plate, and brisket primal cuts.

17. The process of claim 16 further comprising the step of:

(j) measuring the value of at least one standard grading criterium for the rib eye of the carcass, the standard grading criteria selected from the group consisting of the area of the rib eye, the percentage of intramuscular fat in the rib eye, the thickness of a subcutaneous fat layer on the rib eye at pre-determined positions, the average thickness of the subcutaneous fat layer on the rib eye, and the width of the subcutaneous fat layer at a standard grade fat measurement site;

and wherein at least one of the standard grading criteria for the rib eye of the carcass is included as an independent variable in the grading parameter predictive equation provided in step (f).

18. The process of claim 16 wherein the grading parameter of the carcass to be determined is saleable yield of the carcass, and wherein:

in step (e), the sections of the carcass include the rib, loin and plate primal cuts, and the ratios of the area of each of the rib, loin and plate primal cuts to the total area encompassed by the carcass image outline are determined;

in step (h), distances are determined from at least 3 reference points on each of the dorsal and ventral regions of the carcass image outline to the mid-line of the carcass image outline;

in step (i), the width of the carcass image outline is determined at at least two reference points; and, in step (f), the grading parameter predictive equation is a saleable yield predictive equation in which the following are included as independent variables:

the areas of the loin and plate primal cuts;

the ratios of the area of the rib primal cut, the loin primal cut and the plate primal cut to the total area encompassed by the carcass image outline;

distances from at least 3 reference points on each of the dorsal and ventral regions of the carcass image outline to the mid-line of the carcass image outline; and, the width of the carcass image outline at at least two reference points.

19. An apparatus for determining a quality grade of an animal carcass comprising:

(a) image acquisition means for obtaining an image which includes the rib eye of the carcass;

(b) computing and storage means for:

(i) storing the image as an array of pixels providing colour data representative of colour information at the corresponding part of the image;

(ii) discriminating pixels representing muscle tissue from pixels representing fat tissue on the basis of a pixel colour characteristic threshold;

(iii) identifying a cluster of muscle tissue pixels within the image that represents the rib eye and tracing the outline of the rib eye muscle to exclude external image sections representing muscle tissue which abuts but is not part of the rib eye;

(iv) determining the proportion of pixels within the rib eye outline representing fat relative to the total number of pixels within the rib eye outline to obtain a value of the percentage of intramuscular fat in the rib eye;

(v) applying means (i) through (iv) to a plurality of reference images of rib eyes of carcasses of pre-determined quality grade to establish a relationship between the percentage of intramuscular fat in the rib eye and the quality grade of the carcass;

(vi) solving the relationship determined by means (v) for the value of the percentage of intramuscular fat in the rib eye determined by means (iv) to determine the quality grade of the carcass; and (c) means for providing an output of the quality grade of the carcass.

20. The apparatus of claim 19 further comprising computing and storage means for:

(vii) discriminating pixels representing muscle tissue from pixels which do not represent muscle tissue or fat tissue on the basis of a pixel colour saturation level threshold.

21. An apparatus for determining parameters of a rib eye of a carcass, comprising:

(a) image acquisition means for obtaining an image which includes the rib eye of the carcass;

(b) computing and storage means for:

(i) storing the image as an array of pixels providing data representative of information at the corresponding part of the image;

(ii) discriminating pixels representing muscle tissue from pixels representing fat tissue on the basis of a pixel colour characteristic threshold;

(iii) identifying a target cluster of contiguous muscle tissue pixels within the image, the target cluster including the rib eye, and tracing the outline of the cluster of muscle tissue pixels including the rib eye;

(iv) identifying and excising external image sections representing muscle tissue which abuts but is not part of the rib eye, the means for identifying external image sections including:

(a) means for identifying outward turns in the rib eye outline traced by means (iii); and (b) means for rejecting an outward turn as a potential site to commence a cut to excise an external image section if a first line bisecting the turn would not be substantially parallel to a second line tangent to a first generally elliptical figure surrounding the rib eye outline at a point on the elliptical figure collinear with the centre of the elliptical figure and the vertex of the turn; and (c) means for providing an output of the parameters of the rib eye.

22. The apparatus of claim 21, further comprising computing and storage means for:

(iv) (c) plotting a plurality of search lines originating from the vertices of outward turns which were not rejected by means (b), the search lines radiating inwardly through a range of at least about 20° on either side of a line bisecting the turn; recording the number of pixels representing muscle tissue along each search line until a string of at least about 4 consecutive pixels representing fat is detected; and selecting the search line having the fewest pixels representing muscle tissue as a potential path of a cut to excise an external image section.

23. An apparatus for determining grading parameters of a carcass, comprising:

(a) image acquisition means for obtaining an image of a view of the carcass;

(b) computing and storage means for:

(i) storing the image as an array of pixels providing data representative of information at the corresponding part of the image;

(ii) tracing the outline of the image to produce a carcass image outline;

(iii) locating a plurality of first reference points on the carcass image outline, the first reference points representing anatomical features of the carcass, the anatomical features being identified as protrusions or indentations in the carcass image outline;

(iv) locating at least one second reference point on or within the carcass image outline, the second reference points being located at pre-determined positions relative to the first reference points;

(v) dividing the carcass image into a plurality of sections, the boundaries of each section being determined as a function of the position of the first and second reference points, and determining the area of each section;

(vi) providing a grading parameter predictive equation wherein the grading parameter is included as a dependent variable, and at least one area of a section determined in step (v) is included as an independent variable;

(vii) solving the grading parameter predictive equation to provide a value for the grading parameter of the carcass; and, (c) means for providing an output of the grading parameter of the carcass.

24. A process for determining grading parameters of a carcass, comprising the steps of:

(a) obtaining an image which includes the rib eye of the carcass, the image being composed of an array of pixels providing colour data representative of colour information at the corresponding part of the image;

(b) discriminating pixels representing muscle tissue from pixels representing fat tissue on the basis of a pixel colour characteristic threshold;

(c) identifying a cluster of muscle tissue pixels within the image that represents the rib eye and tracing the outline of the rib eye muscle to exclude external image sections representing muscle tissue which abuts but is not part of the rib eye;

(d) determining the proportion of pixels within the rib eye outline representing fat relative to the total number of pixels within the rib eye outline to obtain a value of the percentage of intramuscular fat in the rib eye;

(e) measuring the value of at least one standard grading criterium for the rib eye image, the standard grading criteria selected from the group consisting of the area of the rib eye, the percentage of intramuscular fat in the rib eye, the thickness of a subcutaneous fat layer on the rib eye at pre-determined positions, the average thickness of the subcutaneous fat layer on the rib eye, and the width of the subcutaneous fat layer at its narrowest point;

(f) providing a grading parameter predictive equation wherein the grading parameter is included as a dependent variable, and at least one of the standard grading criteria for the rib eye is included as an independent variable; and, (g) solving the grading parameter predictive equation to provide a value for the grading parameter of the carcass.

25. The process of claim 24 wherein, in step (c), excluding external image sections includes:

(i) identifying outward turns in the rib eye outline traced in step (c); and (ii) rejecting an outward turn as a potential site to commence a cut to excise an external image section if a first line bisecting the turn would not be substantially parallel to a second line tangent to a first generally elliptical figure surrounding the rib eye outline at a point on the ellipse collinear with the centre of the elliptical figure and the vertex of the turn.

26. An apparatus for determining grading parameters of a carcass, comprising:

(a) image acquisition means for obtaining an image which includes the rib eye of the carcass;

(b) computing and storage means for:

(i) storing the image as an array of pixels providing data representative of information at the corresponding part of the image;

(ii) discriminating pixels representing muscle tissue from pixels representing fat tissue on the basis of a pixel colour characteristic threshold;

(iii) identifying a cluster of muscle tissue pixels within the image that represents the rib eye and tracing the outline of the rib eye muscle to exclude external image sections representing muscle tissue which abuts but is not part of the rib eye;

(iv) determining the proportion of pixels within the rib eye outline representing fat relative to the total number of pixels within the rib eye outline to obtain a value of the percentage of intramuscular fat in the rib eye;

(v) measuring the value of at least one standard grading criterium for the rib eye image, the standard grading criteria selected from the group consisting of the area of the rib eye, the percentage of intramuscular fat in the rib eye, the thickness of a subcutaneous fat layer on the rib eye at pre-determined positions, the average thickness of the subcutaneous fat layer on the rib eye, and the width of the subcutaneous fat layer at its narrowest point;

(vi) providing a grading parameter predictive equation wherein the grading parameter is included as a dependent variable, and at least one of the standard grading criteria for the rib eye is included as an independent variable;

(vii) solving the grading parameter predictive equation to provide a value for the grading parameter of the carcass; and, (c) means for providing an output of the grading parameter of the carcass.

27. The apparatus of claim 26 wherein tracing means (iii) includes:

(a) means for identifying outward turns in the rib eye outline traced in step (c); and (b) means for rejecting an outward turn as a potential site to commence a cut to excise an external image section if a first line bisecting the turn would not be substantially parallel to a second line tangent to a first generally elliptical figure surrounding the rib eye outline at a point on the ellipse collinear with the centre of the elliptical figure and the vertex of the turn.

* * * * *